(12) United States Patent
Nishihara et al.

(10) Patent No.: US 8,557,574 B2
(45) Date of Patent: Oct. 15, 2013

(54) FUNGAL GROWTH INHIBITOR

(75) Inventors: Tatsuji Nishihara, Kitakyushu (JP); Sumio Akifusa, Fukuoka (JP)

(73) Assignee: Seikagaku Corporation, Tokyo (JP)

( * ) Notice: Subject to any disclaimer, the term of this patent is extended or adjusted under 35 U.S.C. 154(b) by 988 days.

(21) Appl. No.: 12/278,917

(22) PCT Filed: Feb. 8, 2007

(86) PCT No.: PCT/JP2007/052249
§ 371 (c)(1),
(2), (4) Date: Aug. 8, 2008

(87) PCT Pub. No.: WO2007/091644
PCT Pub. Date: Aug. 16, 2007

(65) Prior Publication Data
US 2010/0168057 A1    Jul. 1, 2010

(30) Foreign Application Priority Data
Feb. 10, 2006 (JP) .................................. 2006-033418

(51) Int. Cl.
*C12N 5/00*    (2006.01)
*C12N 5/02*    (2006.01)

(52) U.S. Cl.
USPC .......... 435/325; 435/373; 435/383; 435/404; 435/408

(58) Field of Classification Search
USPC ....................................................... 535/69.1
See application file for complete search history.

(56) References Cited

U.S. PATENT DOCUMENTS

| 4,746,504 A | 5/1988 | Nimrod et al. |
| 6,348,190 B1 | 2/2002 | Illes et al. |

FOREIGN PATENT DOCUMENTS

| JP | 2-164829 A | 6/1990 |
| JP | 2613605 B2 | 2/1997 |
| JP | 9-315927 A | 12/1997 |
| JP | 10-513165 A | 12/1998 |
| JP | 11-5744 A | 1/1999 |
| JP | 2001-500860 A | 1/2001 |
| JP | 2003-2810 A | 1/2003 |
| JP | 2005-323506 A | 11/2005 |
| WO | WO-9103559 A1 * | 3/1991 |
| WO | 96/23479 A2 | 8/1996 |
| WO | 97/38113 A1 | 10/1997 |
| WO | 00/56344 A1 | 9/2000 |
| WO | WO-2004093887 A1 * | 11/2004 |

OTHER PUBLICATIONS

Lass-Florl et al., Activities of Antifungal Agents against Yeasts and Filamentous Fungi: Assessment according to the Methodology of the European Committee on Antimicrobial Susceptibility Testing; Antimicrobial Agents and Chemotherapy, vol. 52, No. 10, pp. 3637-3641, 2008.*
Lee et al., Delivery of a vector encoding mouse hyaluronan synthase 2 via crosslinked hyaluronan film; Biomaterials, vol. 26, pp. 1585-1593, 2005.*
Klotz, Adherence of *Candida albicans* to components of the subendothelial extracellular matrix; FEMS Microbiol Let, vol. 68, pp. 249-254, 1990.*
Kingston, Introduction of DNA into Mammalian Cells: Introduction; Current Protocols in Molecular Biology, supplement 64, 9.0.1-9.0.5, 2003.*
Kim et al., Delivery of a vector encoding mouse hyaluronan synthase 2 via crosslinked hyaluronan film; Biomaterials, vol. 26, pp. 1585-1593, 2005 (erroneously cited as 'Lee et al.' in previous action).*
McDonald et al., Hyaluronan: Genetic insights into the complex biology of a simple polysaccharide; Glycoconjugate Journal, vol. 19, pp. 331-339, 2003.*
Payman Pirnazar, et al.; "Bacteriostatic Effects of Hyaluronic Acid", J. Periodontal, Apr. 1999, vol. 70, No. 4; pp. 370-374.
Tang Z.H., et al.; 2002; Zhongguo Xiu Fu Chong Jiam Wai Ke Za Zhi; Jul. 2002, vol. 16 No. 4; pp. 259-261.
Eduardo O. Melo et al., "Animal transgenesis: state of the art and applications", Journal of Applied Genetics, 2007, 48(1): 47-61.
Meijun Sakai et al., "Growth suppressive effect of macromolecular hyaluronic acid on *Candida albicans*", Japanese Journal of Bacteriology, 2004, 59(1): p. 207, Abstract 2109.
Eckhard Wolf et al., "Transgenic technology in farm animals—progress and perspectives", Experimental Physiology, 2000, 85(6): 615-625.
The Japanese Patent Office , Office Action dated Jul. 31, 2012, in counterpart Japanese Application No. 2007-557890.

* cited by examiner

*Primary Examiner* — Celine Qian
*Assistant Examiner* — Addison D Ault
(74) *Attorney, Agent, or Firm* — Sughrue Mion, PLLC

(57) ABSTRACT

A very safe and useful agent for inhibiting fungal growth and the like are provided by the present invention. Specifically, the present invention provides (1) an agent for inhibiting fungal growth comprising hyaluronic acid or a salt thereof excluding a heavy metal salt as the active ingredient, and a method for inhibiting fungal growth, which comprises at least a step of allowing hyaluronic acid or a salt thereof excluding a heavy metal salt to contact with a fungus, (2) an agent for reinforcing activity of inhibiting fungal growth possessed by a cell, which comprises a DNA encoding a hyaluronic acid synthase as the active ingredient, (3) a method for reinforcing activity of inhibiting fungal growth of a cell, which comprises at least a step of transfecting a DNA encoding a hyaluronic acid synthase into the cell, and (4) a method for inhibiting fungal growth, which comprises at least a step of allowing a cell transfected with a DNA encoding a hyaluronic acid synthase to contact with a fungus.

6 Claims, 5 Drawing Sheets

FUNGAL GROWTH INHIBITOR

TECHNICAL FIELD

The present invention relates to an agent for inhibiting fungal growth comprising hyaluronic acid or a salt thereof excluding heavy metal salts as the active ingredient.

BACKGROUND OF THE INVENTION

Firstly, the abbreviations used in this specification are described.
HA: hyaluronic acid
HAS: hyaluronic acid synthase
The following describes on the techniques related to the present invention.

Patent Reference 1 and Patent Reference 2 disclose a heavy metal salt of HA, wherein the metal is selected from silver, gold, cerium and tungsten, and a method for inhibiting growth of a microorganism, which comprises allowing the microorganism to contact with an effective amount of silver HA. Additionally, it is described that the silver HA inhibits growth of *Candida albicans* and *Candida tropicalis*.

Patent Reference 3 and Patent Reference 4 disclose pharmaceutical compositions having anti-microbial activity, which comprise an HA-zinc associated compound (complex) or an HA-cobalt associated compound (complex) as the active ingredient. Also, it is described that although a zinc HA solution induced several figures of reduction of a large number of organisms tested (including *Candida albicans* and *Aspergillus niger*), the number of the organisms tested did not change significantly in a sodium HA. Additionally, it is described also that the sodium HA solution did not show its inhibitory effect upon any one of the organisms tested even when the concentration is 2000 μg/mL.

Patent Reference 5 and Patent Reference 6 disclose the use of one compound or several compounds selected from the group consisting of carbohydrates or carbohydrate derivatives, as the anti-adhesive active ingredient for a microorganism or the like. Additionally, HA is described as an example of the carbohydrates, and a fungus, *Candida albicans* or the like is described as an example of the microorganism. However, there is no disclosure on the specific pharmacological test result of their drug effect, and it is not described clearly that the method can be used.

Although non-patent Reference 1 discloses on the bacteriostatic activity of HA, there is no description or suggestion regarding fungi and the genus *Candida*.

There is a description in Non-patent Reference 2 on the bacteriostatic test (including *Candida albicans*) of sodium HA. However, it is concluded as a result that sodium HA does not have the bacteriostatic activity since the microorganisms properly grew in a medium containing sodium HA.

Patent Reference 1: Japanese Patent No. 2613605
Patent Reference 2: U.S. Pat. No. 4,746,504
Patent Reference 3: JP-T-2001-500860
Patent Reference 4: U.S. Pat. No. 6,348,190
Patent Reference 5: JP-T-10-513165
Patent Reference 6: International Publication WO 96/23479
Non-patent Reference 1: Pimazar P. et al., 1999, Journal of Periodontology, vol. 70, no. 4, p. 370-374
Non-patent Reference 2: Tang Z. H. et al., 2002, Zhongguo Xiu Fu Chong Jiam Wai Ke Za Zhi, vol. 16, no. 4, p. 259-261

DISCLOSURE OF THE INVENTION

Problems that the Invention is to Solve

The object of the present invention is providing a markedly safe and useful agent for inhibiting fungal growth and the like,

Means for Solving the Problems

The inventors of the present invention have intensively carried out examinations for the purpose of solving the problems described in the above and found as a result that HA or a salt thereof (excluding heavy metal salts) has the activity of significantly inhibiting growth of fungi, and accomplished the present invention. Additionally, the inventors have found that the activity of inhibiting fungal growth possessed by a cell can be reinforced by transfecting a DNA encoding HAS into the cell, and accomplished the present invention.

Namely, the present invention provides an agent for inhibiting fungal growth which uses HA or a salt thereof (excluding heavy metal salts; to be referred to as same hereinafter) as the active ingredient.

Weight average molecular weight of the HA or a salt thereof as the active ingredient of the inhibitor of the present invention is preferably from 60,000 to 2,500,000, more preferably from 100,000 to 2,500,000, further preferably from 200,000 to 2,500,000, further preferably from 250,000 to 2,500,000, further preferably from 500,000 to 2,500,000, further preferably from 750,000 to 2,500,000, further preferably from 800,000 to 2,500,000, further preferably from 1,000,000 to 2,500,000, further preferably from 1,500,000 to 2,500,000, particularly preferably from 1,800,000 to 2,200,000.

It is preferable that the inhibitor of the present invention is used under a state of solution when it is allowed to contact with a fungus. In that case, the concentration of HA or a salt thereof when it is allowed to contact with a fungus is preferably from 0.1 mg/mL to 5 mg/mL, more preferably from 0.1 mg/mL to 2 mg/mL, further preferably from 0.5 mg/mL to 2 mg/mL, further preferably from 0.5 mg/mL to 1.5 mg/mL, particularly preferably from 0.8 mg/mL to 1.2 mg/mL.

Additionally, it is preferable that the fungus as the object of the growth, inhibition by the inhibitor of the present invention is 1 or 2 or more fungi selected from the group consisting of those which belong to the genus *Candida*, those which belong to the genus *Aspergillus*, those which belong to the genus *Cryptococcus*, those which belong to the genus *Histoplasma*, those which belong to the genus *Trichophyton*, those which belong to the genus *Microsporum*, those which belong to the genus *Malassezia*, those which belong to the genus *Coccidioides*, those which belong to the genus *Blastomyces* and those which belong to the genus *Mucor*.

The present invention also provides a method for inhibiting fungal growth, which comprises at least a step of allowing HA or a salt thereof to contact with a fungus (to be referred to as "inhibition method 1 of the present invention" hereinafter).

The present invention also provides an agent for reinforcing activity of inhibiting a fungal growth possessed by a cell, which comprises a DNA encoding HAS (to be referred to as "reinforcing agent of the present invention" hereinafter).

It is preferable that the reinforcing agent of the present invention is used by transfecting it into a cell. Also, it is preferable that the "HAS" is 1 or 2 or more of HAS selected from the group consisting of HAS 1, HAS 2 and HAS 3. Also, it is preferable that the "cell" is an epithelial cell or a fibroblast.

The present invention also provides a method for reinforcing activity of inhibiting fungal growth of a cell, which comprises at least a step of transfecting a DNA encoding HAS into the cell (to be referred to as "reinforcing method of the present invention" hereinafter).

Additionally, the present invention also provides a method for inhibiting fungal growth, which comprise at least a step of allowing a cell transfected with a DNA encoding HAS 0 contact with a fungus (to be referred to as "inhibition method 2 of the present invention" hereinafter).

Effect of the Invention

The inhibitor of the present invention and inhibition method 1 of the present invention are markedly useful, since they can significantly inhibit growth of fungi and safety of the active ingredient (HA or a salt thereof) is also markedly high. Also, the reinforcing agent and reinforcing method of the present invention are markedly useful, since they can strongly reinforce activity of inhibiting the fungal growth possessed by a cell. Additionally, the inhibition method 2 of the present invention is markedly useful since fungal growth can be significantly inhibited by applying the reinforcing agent and reinforcing method of the present invention.

BEST MODE FOR CARRYING OUT THE INVENTION

Figure 1:
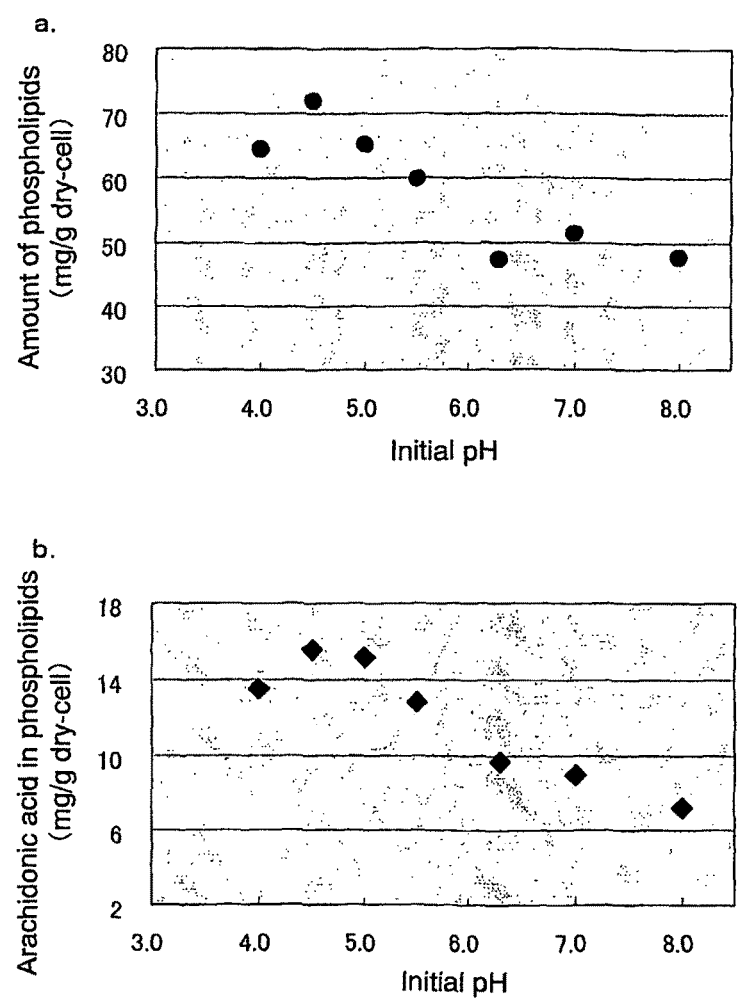
FIG. 1 is a graph showing activity of inhibiting *Candida* growth by an epithelial cell.

The following describes the present invention in detail based on the best mode for carrying out the present invention.
<1> The Inhibitor of the Present Invention The inhibitor of the present invention is an agent for inhibiting fungal growth comprising HA or a salt thereof as the active ingredient,
(1) Active Ingredient Origin of the HA or a salt thereof which can be used as the active ingredient of the inhibitor of the present invention is not particularly limited, and those which were separated from a chicken crest, an umbilical cord, an HA-producing microorganism and the like can be used.

Also, its purity and the like are not particularly limited and can be optionally selected according to the case, object, region and the like of requiring inhibition of fungal growth. For example, when the object is to inhibit fungal growth on the tissues and the like in the living body or the region or case where high degree asepticness and cleanliness are required including the case of a cell culture and a tissue culture and the like, it is preferable to use those which are highly purified and sterilized. Additionally, in case of applying to the inside of a living body, it is preferable to use those which do not substantially contain medically unacceptable substances (e.g., endotoxin and the like).

Also, when the object is to inhibit fungal growth in the mouse, gullet and the like digestive tracts or on the vagina, skin, eye and the like extra-living body tissues, although it is preferable to use HA purified to a high purity, there is no harm in some cases in using those having a slightly low purity. Additionally, when the object is to inhibit fungal growth in substances other than the living body, although it is also preferable to use HA purified to a high purity, those having a low purity can also be used according to the purpose, case and the like.

Additionally, the "salt of HA" is not particularly limited too, as long as it is other than the "heavy metal salts of HA", and can be optionally selected by those skilled in the art. For example, when the object is to inhibit fungal growth in the living body, a medically acceptable salt can be selected.

In this connection, the "heavy metal" according to the instant application documents means a metal having a density of 4 g·cm$^{-3}$ or more. Accordingly, those skilled in the art can easily understand which metals come under the heavy metals based on the definition. Examples of the heavy metal include silver, gold, cerium, tungsten, zinc and cobalt.

Examples of the salt of HA which can be used as the active ingredient of the inhibitor of the present invention include salts with inorganic bases such as an alkali metal salt (lithium salt, sodium salt, potassium salt or the like), an alkaline earth metal salt (beryllium salt, magnesium salt, calcium salt or the like) and an ammonium salt, or salts with organic bases such as diethanolamine salt, cyclohexylamine salt and an amino acid salt. Among them, salts with inorganic bases are preferable. Among the salts with inorganic bases, alkali metal salts or alkaline earth metal salts are preferable, and alkali metal salts are more preferable. Among the alkali metal salts, sodium salt is preferable.

Weight average molecular weight of the HA or a salt thereof which can be used as the active ingredient of the inhibitor of the present invention is not particularly limited too. It can be optionally selected according to the purpose and the like. An example the weight average molecular weight of HA or a salt thereof is a range of from 60,000 to 2,500,000. Particularly, it is preferably from 100,000 to 2,500,000, more preferably from 200,000 to 2,500,000, further preferably from 250,000 to 2,500,000, further preferably from 500,000 to 2,500,000, further preferably from 750,000 to 2,500,000, further preferably from 800,000 to 2,500,000, further preferably from 1,000,000 to 2,500,000, further preferably from 1,500,000 to 2,500,000, particularly preferably from 1,800,000 to 2,200,000.

In this connection, the weight average molecular weight of the HA or a salt thereof which can be used as the active ingredient of the inhibitor of the present invention can be obtained by measuring its limiting viscosity in accordance with The Pharmacopoeia of Japan, 13$^{th}$ revision: the 36$^{th}$ item of General Testing Methods, Viscosity measuring method, and calculating it by the formula of Laurent et al. (Biochim. Biophys. Acta, 42, 476 (1960)).

By the use of such an HA or a salt thereof as the active ingredient, it can be made into the inhibitor of the present invention having markedly excellent effects.
(2) Dosage Forms and the Like of the Inhibitor of the Present Invention Dosage forms and the like of the inhibitor of the present invention are not particularly limited as long as it contains HA or a salt thereof as the active ingredient and its fungal growth inhibitory effect is exerted.

In this connection, it is preferable to use the inhibitor of the present invention under a state of solution when it is allowed to contact with fungi. Accordingly, the forms of the inhibitor of the present invention can be selected from various dosage forms which can be made into a state of solution at the time of its use (when it is allowed to contact with fungi)

For example, the inhibitor of the present invention may be used as preparations of a state of solution containing HA or a salt thereof, or as powders, granules and the like solid preparations to be dissolved when it is used. Additionally, when it is provided as the preparations of a state of solution for example, it may be provided under a frozen state or as the solution as such.

According to the inhibitor of the present invention, the concentration of HA or a salt thereof when it is allowed to contact with a fungus is preferably from 0.1 mg/mL to 5 mg/mL. Particularly, said concentration is preferably from 0.1 mg/mL to 2 mg/mL, more preferably from 0.5 mg/mL to 2 mg/mL, further preferably from 0.5 mg/mL to 1.5 mg/mL, particularly preferably from 0.8 mg/mL to 1.2 mg/mL.

Accordingly, the amount of HA or a salt thereof contained in the inhibitor of the present invention is not particularly limited, as long as it is an amount that the aforementioned concentration can be obtained when it is used (when it is allowed to contact with fungi), and can be optionally selected according to the purpose, dosage form and the like.

For example, when the object is inhibiting fungal growth in the living body (excluding body fluids) or in substances other than living body (excluding liquids), and when the inhibitor of the present invention is made into a preparation of a state of solution, the concentration of HA or a salt thereof in said preparation can be set to the same concentration as described above (e.g., from 0.1 mg/ml, to 5 mg/mL).

Additionally, when the object is inhibiting fungal growth in a body fluid or a substance of a liquid state, and when the inhibitor of the present invention is made into a preparation of a state of solution, the HA or a salt thereof in said preparation can be set to be a concentration of higher than the aforementioned concentration. Specifically, a concentration may be selected to be such that HA or a salt thereof becomes the same concentration as described in the above (e.g., from 0.1 mg/mL to 5 mg/mL) when this is allowed to contact (mix or the like) with a body fluid or a substance of a liquid state.

The inhibitor of the present invention can be distributed, preserved or used by filling it in an appropriate container such as an ampul, a vial, a bottle, a syringe or the like.

Conventionally known methods can be used in preparing the inhibitor of the present invention. Additionally, other fungal growth inhibitory components and a stabilizer, an emulsifying agent, an osmotic pressure adjusting agent, a buffer agent, a tonicity agent, a corrective agent, a preservative, a pH adjusting agent, a soothing agent, a coloring agent, an excipient, a binder, a lubricant, a disintegrator and the like other components can be blended in making the pharmaceutical preparation, as long as they do not exert bad influence upon HA or a salt thereof and they do not exert influence upon the effects of the present invention.

Although the inhibitor of the present invention can be produced as described above, a commercial product containing HA or a salt thereof may be directly used as the inhibitor of the present invention. Examples of the commercial products include a mouth washing liquid "Kinsui" (Registered trademark) (manufactured by Seikagaku Corporation). The product is an aqueous solution of sodium HA and contains a corrective (xylitol), preservatives (sodium benzoate and potassium sorbate) and pH adjusting agents (disodium hydrogenphosphate and sodium dihydrogenphosphate) as the other components.

(3) Application Object, Using Method and the Like of the Inhibitor of the Present Invention The inhibitor of the present invention can be used for the inhibition of fungal growth in every substance including the living body. Accordingly, the substance to which the inhibitor of the present invention is applied is not particularly limited, as long as it is a substance in which a fungus whose growth should be inhibited is already present, a substance in which it must be present in the future or a substance having such possibilities. Examples of the substance to which the inhibitor of the present invention is applied include non-organism bodies (e.g., an industrial product, a culture medium and the like), organism bodies (e.g., an animal, a plant and the like) and the. Particularly, it is preferable that the substance is a culture medium or an organism body.

It is preferable that the culture medium is a culture medium of an animal cell. It is preferable that the animal cell is an epithelial cell or a fibroblast.

As the organism body, an animal is preferable. Among the living body of an animal, an animal tissue is preferable and an epithelial tissue is more preferable. Examples of the epithelial tissue include epithelia in the digestive tracts (inside of the buccal cavity, inside of the gullet, inside of the stomach, inside of the duodenum, inside of the small intestines, inside of the large intestine and the like), epithelia on the surface of various organs (the heart, the lungs, the liver, the spleen, the kidney and the like), epithelia of the skin and an eye, epithelia of various cavities (inside the ear cavity, inside the nasal cavity and the like), epithelia of inside the urinary organs (inside of the urethra, inside of the bladder and the like), epithelia of inside of the reproductive organs (inside of the vagina, inside of the uterus and the like) and the like. Particularly, a mucosal epithelium is preferable. Although kinds and the like of the mucosal epithelium are not particularly limited too, the mucosal epithelium inside of the digestive organs is preferable. Particularly, the intrabuccal epithelium is more preferable.

The inhibitor of the present invention can be used in the inhibition of fungal growth in any one of these substances.

The "fungus" as the object of growth inhibition by the inhibitor of the present invention is not particularly limited as long as it belongs to fungi. Examples of such a fungus include 1 or 2 or more fungi selected from the group consisting of those which belong to the genus *Candida*, those which belong to the genus *Aspergillus*, those which belong to the genus *Cryptococcus*, those which belong to the genus *Histoplasma*, those which belong to the genus *Trichophyton*, those which belong to the genus *Microsporum*, those which belong to the genus *Malassezia*, those which belong to the genus *Coccidioides*, those which belong to the genus *Blastomyces* and those which belong to the genus *Mucor*.

It is preferable to use the inhibitor of the present invention for the growth inhibition of particularly the fungus belonging to the genus *Candida*. Examples of the fungi which belong to the genus *Candida* include *Candida albicans, Candida glabrata, Candida krusei* and *Candida tropicalis* and the like.

The method for using the inhibitor of the present invention is not particularly limited, as long as it is used in such an embodiment that the molecule of HA or a salt thereof as the active ingredient of the inhibitor of the present invention contacts with a fungus, and can be optionally set according to the substance to which the inhibitor of the present invention is applied (a substance for which inhibition of fungal growth is desired), the case, the object and the like.

For example, when the substance for which inhibition of fungal growth is desired is in a liquid state, the molecule of HA or a salt thereof can be contacted with the fungus by the addition or the like of the inhibitor of the present invention.

Also, when the substance for which inhibition of fungal growth is desired is in a solid state, it may be used by an embodiment in which this is coated with the inhibitor of the present invention. In that case, the substance for which inhibition of fungal growth is desired and the inhibitor of the present invention may be firstly allowed to contact with each other, by soaking the substance for which inhibition of fungal growth is desired in the inhibitor of the present invention or pouring or spraying the inhibitor of the present invention into or to said substance, subsequently allowing said inhibitor to flow by stirring, shaking or the like physical stimulus.

For example, gargling may be carried out with using the inhibitor of the present invention in order to inhibit fungal growth in the buccal cavity. In such a manner, using method of the inhibitor of the present invention can be optionally set according to its purpose and the like.

Additionally, when more effective inhibition of fungal growth is desired, the above-mentioned operation and action may be carried out repeatedly.

The using amount per once, using interval and the like of the inhibitor of the present invention are not particularly limited, since these are items which should be individually decided according to the substance for which inhibition of fungal growth is desired, case, object and the like. For example, when it is necessary to inhibit growth of more fungi within a short period of time, the using amount of the inhibitor of the present invention per once may be increased or the aforementioned operation and action may be carried out repeatedly within a short period of time. For example, when the inhibitor of the present invention is administered to human, HA or a salt thereof can be administered generally at a dose of approximately from 5 mg to 1,000 mg per adult and at a frequency of from 1 to several times per day.

The fungal growth inhibitory effect of the inhibitor of the present invention can be confirmed by the method which is described later in Examples.

<2> Inhibition Method 1 of the Present Invention

The inhibition method 1 of the present invention is a method for inhibiting fungal growth, which comprises at least one step of allowing HA or a salt thereof to contact with a fungus.

Description on the HA or a salt thereof which can be used herein is identical to the aforementioned <1>. Accordingly, it is necessary that the "salt of HA" to be used in the inhibition method 1 of the present invention is other than "heavy metal salts of HA".

Additionally, all of the contacting method of "HA or a salt thereof" with a fungus, the concentration of "HA or a salt thereof" at the time of the contact, the substance as the object of the application, the fungus as the object of growth inhibition and the like are identical to the aforementioned <1>. It should be understood that the inhibition method of the present invention can be carried out by the same method of the using method of the inhibitor of the present invention.

In this connection, the inhibition method 1 of the present invention may further comprise other steps, as long as it comprises at least one step of allowing HA or a salt thereof to contact with a fungus. For example, a step for removing or sterilizing the fungus after allowing HA and a salt thereof to contact with the fungus, a step for removing HA or a salt thereof after allowing HA or a salt thereof to contact with the fungus, and the like may be further contained. As a matter of course, the step of allowing HA or a salt thereof to contact with a fungus may be carried out repeatedly.

The fungal growth inhibitory effect by the inhibition method 1 of the present invention can be confirmed by the method which is described later in Examples.

<3> Reinforcing Agent of the Present Invention

The reinforcing agent of the present invention is an agent for reinforcing the activity for inhibiting fungal growth possessed by a cell, which uses a DNA encoding HAS as the active ingredient.

(1) Active Ingredient

The "DNA encoding HAS" which can be used as the active ingredient of the reinforcing agent of the present invention is not particularly limited with as long as it encodes a polypeptide having the HAS activity and also is a DNA having the ability to express said polypeptide. It is preferable that this DNA is a cDNA.

The organism species and the like from which the HAS encoded by the DNA is originated are not particularly limited and can be optionally selected by those skilled in the art according to the object and the like.

For example, one species of HAS (*Streptococcus hyalyticum*-derived has-A) has been found in a bacterium, and a HAS, DG 42, in *Xenopus*, and three species of HAS (HAS 1, 2 and 3) in mammals. HAS 1 is disclosed in Biochem. Biophys. Res. Commun., 222, pp. 816-820 (1996), and HAS 2 and HAS 3 in Genomics, 41(3), pp. 493-497 (1997), respectively. Additionally, regarding the DNA (cDNA) encoding HAS 2 for example, a human-derived counterpart is disclosed in J. Biol. Chem., 271(38), pp. 22945-22948 (1996), and a mouse-derived counterpart in J. Biol. Chem., 271(38), pp. 23400-23406 (1996), respectively.

As the active ingredient of the reinforcing agent of the present invention, a DNA encoding any one of these HAS can also be used. Additionally, these DNA to which a modification and the like were added can also be used in the same manner, as long as the polypeptide encoded by the DNA after its modification keeps the HAS activity.

Particularly among these, it is preferable to use a DNA encoding one or two or more HAS selected from the group consisting of HAS 1, HAS 2 and HAS 3.

In this connection, although the DNA molecules coding for mouse-derived HAS 1, HAS 2 and HAS 3 are respectively shown in SEQ ID NOs:1, 2 and 3, the DNA which can be used as the active ingredient of the reinforcing agent of the present invention is not limited thereto.

The DNA molecules encoding these HAS can be produced by conventionally known methods.

The "DNA molecules encoding HAS" as the active ingredient of the reinforcing agent of the present invention may be used under a state of being kept in a vector or the like. In that case, it is preferable to use it by keeping in an expression vector.

As the method for keeping the "DNA encoding HAS" in a vector or the like, a general genetic engineering technique for transfecting a DNA into a vector can be used.

As the vector for transfecting the "DNA encoding HAS" therein, for example, an appropriate expression vector (a phage vector or plasmid vector) which can effect expression of the transfected DNA can be used, and it can be optionally selected according to the host cell into which the vector is transfected.

(2) Dosage Forms and the Like of the Reinforcing Agent of the Present Invention

Dosage forms and the like of the reinforcing agent of the present invention and the like are not particularly limited as long as the DNA coding for HAS is contained as the active ingredient.

The reinforcing agent of the present invention can be used by transfecting it into a cell. Accordingly, it can be optionally selected from various dosage forms having such a function that when the reinforcing agent of the present invention is transfected into a cell, the "DNA encoding HAS" as the active ingredient enters into the cell, HAS is thereby expressed in said cell and HAS is produced in said cell.

For example, the reinforcing agent of the present invention may be used as preparations of a state of solution containing a DNA encoding HAS, or as powders, granules and the like solid preparations to be dissolved when it is used. Additionally, when it is provided as the preparations of a state of solution for example, it may be provided under a frozen state or as the solution as such. Accordingly, as the dosage form of the reinforcing agent of the present invention, it should be understood that an embodiment similar to that of a general vector or plasmid for transfection into cells can be used.

Amount of the "DNA encoding HAS" to be contained in the reinforcing agent of the present invention can be optionally selected by those skilled in the art according to the cell into which the reinforcing agent of the present invention is transfected, various conditions in transfecting it and the like.

The reinforcing agent of the present invention can be distributed, preserved or used by filling it in an appropriate container such as an ampul, a vial, a tube or the like.

Conventionally known methods can be used in preparing the reinforcing agent of the present invention. Additionally, other components such as a stabilizer, a buffer agent, a preservative, a pH adjusting agent, a coloring agent and a filler can be blended in making the pharmaceutical preparation, as long as they do not exert bad influence upon the DNA encoding HAS and also do not exert influence upon the effects of the present invention.

Although the reinforcing agent of the present invention can be produced as described in the above, the "DNA encoding HAS" may be directly used as the reinforcing agent of the present invention.

(3) Using Method and the Like of the Reinforcing Agent of the Present Invention

The reinforcing agent of the present invention can be used for the purpose of reinforcing activity of inhibiting the fungal growth possessed by a cell.

As is shown in Examples which are described later, the inventors of the present invention have found that a cell (e.g., an epithelial cell, fibroblast or the like) is possessed of activity of inhibiting the fungal growth. The purpose of the reinforcing agent of the present invention is to exert further higher activity of inhibiting fungal growth by reinforcing activity of inhibiting the fungal growth possessed by the cell.

The reinforcing agent of the present invention can be used for all of the cells which have activity of inhibiting the fungal growth. As such cells, the cells described as examples in the aforementioned <1> (3) and the cells derived from various epithelial cells described as examples in the aforementioned <1> (3) are preferable. Please see the aforementioned <1> (3) for their detailed descriptions.

Namely, it is preferable that the reinforcing agent of the present invention is used for the purpose of reinforcing the activity of inhibiting fungal growth of animal cells. Particularly, it is preferable to use it in epithelial cells and fibroblasts. Additionally, conditions of the cell when the reinforcing agent of the present invention is applied thereto are not particularly limited too, and it may be in the state of a culture mixture or in such a state that it is present in a living body tissue.

Specific examples of the epithelial cell include epithelial cells in the digestive organs (inside of the buccal cavity, inside of the gullet, inside of the stomach, inside of the duodenum, inside of the small intestines, inside of the large intestine and the like), epithelial cells on the surface of various organs (the heart, the lungs, the liver, the spleen, the kidney and the like), skin cell, epithelial cell of an eye, epithelial cells of various cavities (inside of the ear cavity, inside of the nasal cavity and the like), epithelial cells of inside of the urinary organs (inside of the urethra, inside of the bladder and the like), epithelial cells of inside of the reproductive organs (inside of the vagina, inside of the uterus and the like) and the like. Particularly, a mucosal epithelial cell is preferable. Although kinds and the like of the mucosal epithelial cell are not particularly limited too, the mucosal epithelial cells inside of the digestive organs are preferable. Particularly, the intrabuccal epithelial cell is more preferable. Similar to the case of epithelial cells, various kinds of fibroblast can also be used.

Contents of the "activity of inhibiting fungal growth" as the object of the reinforcement by the reinforcing agent of the present invention is not particularly limited too, as long as it is the activity of inhibiting fungal growth. Description of the "fungus" as used herein is the same as the aforementioned <1>.

The using method of the reinforcing agent of the present invention is not particularly limited, as long as the "DNA encoding HAS" as the active ingredient of the reinforcing agent of the present invention can be transfected into a cell keeping the activity of inhibiting fungal growth, and can be optionally set according to the cell to be the object of application of the reinforcing agent of the present invention, the case, the object and the like. For example, the methods which are similar to the general genetic engineering techniques which are used in the gene transfection into cell (transformation of cell) can be used.

More specifically, it can be achieved by carrying out the operations of allowing the reinforcing agent of the present invention to contact with a cell and then transfecting a DNA (active ingredient of the reinforcing agent of the present invention) into said cell.

The operation of transfecting the DNA into a cell, a method which uses a commercially available transfection reagent, a DEAE-dextran method, an electroporation method and the like can be used. By the use of the reinforcing agent of the present invention in such manner, the activity of inhibiting fungal growth possessed by the cell can be reinforced.

The effect of the reinforcing agent of the present invention to reinforce activity of inhibiting fungal growth can be confirmed by the method described in Examples which are described later.

<4> Reinforcing Method of the Present Invention

The reinforcing method of the present invention is a method for reinforcing activity of inhibiting fungal growth of a cell, which comprises at least a step of transfecting a DNA encoding HAS into the cell.

Description on the "DNA encoding HAS" which can be used herein is the same as in the aforementioned <3>.

Additionally, descriptions on the transfecting method of the "DNA encoding HAS" into a cell, the "cell" into which the DNA is transfected and the like are also the same as in the aforementioned <3>. It should be understood that the reinforcing method of the present invention can be carried out by a method which is similar to the using method of reinforcing agent of the present invention in the aforementioned <3>.

In this connection, the reinforcing method of the present invention may further comprise other steps as long as it comprises at least a step of transfecting a DNA encoding HAS into the cell. For example, it may further comprise a step for allowing a cell to grow after the transfection of a DNA encoding HAS into the cell, a step for allowing the cell to contact with a fungus after the transfection of a DNA encoding HAS into the cell, and the like.

The effect of the reinforcing method of the present invention to reinforce activity of inhibiting fungal growth can be confirmed by the method described in Examples which are described later.

<5> Inhibition Method 2 of the Present Invention

The inhibition method 2 of the present invention is a method for inhibiting fungal growth, which comprises at least a step of allowing a cell transfected with a DNA encoding HAS to contact with a fungus.

As the "cell transfected with a DNA encoding HAS", for example, the cell treated with the reinforcing agent of the present invention in the aforementioned <3>, or the cell which passed the "step for transfecting a DNA encoding HAS into a cell" in the aforementioned <4> can be used as such. Accordingly, the description on the "cell" transfected with a DNA encoding HAS is the same as in the aforementioned <3> and <4>. Additionally, the description on the "fungus" to be contacted is also the same as in the aforementioned <3> and <4>.

The method for contacting the "cell transfected with a DNA encoding HAS" with a fungus is not particularly limited, as long as it is an embodiment of contacting said cell with a fungus, and can be carried out by a method which is similar to the using method of the inhibitor of the present invention in the aforementioned <1>, according to the case, purpose and the like.

In this connection, the inhibition method 2 of the present invention may further comprise other steps, as long as it comprises at least a step of allowing a cell transfected with a DNA encoding HAS to contact with a fungus. For example, a step for removing the fungus after allowing the cell transfected with a DNA encoding HAS to contact with the fungus, a step for removing a cell after allowing said cell transfected with a DNA encoding HAS to contact with a fungus, and the like may be further contained. As a matter of course, the step of allowing a cell transfected with a DNA encoding HAS to contact with a fungus may be carried out repeatedly.

When more effective inhibition of fungal growth is desired, amount of the "cell transfected with a DNA encoding HAS" to be used may be increased, or the step of allowing the cell transfected with a DNA encoding HAS to contact with a fungus may be carried out repeatedly.

The effect of the inhibition method 2 of the present invention to inhibit fungal growth can be confirmed by the method described in Examples which are described later.

EXAMPLES

Although the following describes the present invention further illustratively based on examples, the technical scope of the present invention is not limited thereby.

(1) Materials and Methods

Firstly, the materials and methods used in the examples are described.

(1-1) Cell Culture

A human buccal epithelial cell strain KB (ATCC (American Type Culture Collection) catalog number: CCL-17) and COS-7 cell (a cell obtained by transforming a *Cercopithecus aetiopus*-derived kidney cell with simian virus 40 (to be referred to as "SV40" hereinafter)) were kept at 37° C. in 90% Eagle's minimum essential medium (to be referred to a "DMEM" hereinafter) (manufactured by Sigma) containing 10% fetal calf serum (to be referred to as "FCS" hereinafter), 1% penicillin/streptomycin (both manufactured by Gibco), non-essential amino acid and Earle's balanced salt solution, under a condition of 5% $CO_2$ and sub-cultured at intervals of 3 to 4 days. Regarding a gingival epithelium (GE) 1 cell strain (GE 1 cell strain), a cell established from a C57BL/6 mouse GE tissue transfected with a temperature-sensitive SV40 large T antigen gene (J. Oral Pathol. Med., 30(5), p. 296-304 (2001)) was cultured using a plastic dish at 33° C. in SFM 101 (manufactured by Nissui Pharmaceutical) containing 1% FCS and 10 ng/mL EGF. Calcium concentration of the SFM 101 medium was 1.13 mM. The cell proliferated exponentially and reached a confluent state on the 10th day after the culturing to form a three dimensional structure consisting of layered epithelia.

(1-2) HA

The HA used (tetradecasaccharide, weight average molecular weight 60 kDa, 250 kDa, 800 kDa or 2,000 kDa) was obtained from Central Research Laboratories, Seikagaku Corporation.

(1-3) Target Fungi

As the fungi, various *Candida* species (*C. albicans* ATCC 18804, *C. glabrata* ATCC 2001, C, krusei ATCC 6258 and *C. tropicalis* ATCC 4563) were used. Each of these *Candida* species was grown on *Candida* GE agar (manufactured by Nissui Pharmaceutical) under a condition of 25° C., and one of the resulting colonies was inoculated into 10 mL of Glucose Peptone broth (manufactured by Nissui Pharmaceutical, to be referred to as "GP broth" hereinafter). The culture mixture was shaken at 25° C. for 1.8 hours to effect its growth until steady state.

(1-4) Treatment of Epithelial Cell (1-4-1) Removal of HA from Cell Matrix

The cells were treated using hyaluronidase (manufactured by Sigma) (50 units/$10^6$ cells) at 37° C. for 2 hours (J. Oral Sci., 45, p. 85-91 (2003)). The cells after the treatment were washed twice with phosphate buffered saline (pH 7.2, to be referred to as "PBS" hereinafter) and re-suspended in DMEM.

(1-4-2) Transfection

Using a 24 well plate, the cells were allowed to grow until they reach a confluence of 90%. DNA (0.8 µl in 50 µl of solution) and Lipofectamine™ (2.0 µl in 50 µl of solution) (manufactured by Invitrogen) were separately diluted with serum-free DMEM, and mixed followed by incubation at room temperature for 20 minutes. To a mixture of the cells and medium, 100 µL of the thus obtained DNA-Lipofectamine™ complex was added. The cells were incubated at 37° C. for 36 hours. In order to effect excess production of HA on the cell surface, a plasmid integrated with a cDNA encoding each isoform of a mouse-derived HAS (pEXneo-HAS 1, pEXneo-HAS2 or pEXneo-HAS3) (J. Biol. Chem., 274(38), p. 25085-25092 (1999)) was used as the expression vector. Nucleotide sequences of the cDNA molecules encoding the mouse-derived HAS 1, HAS 2 and HAS 3 are respectively shown in SEQ ID NO:1, SEQ ID NO:3 and SEQ ID NO:5. Additionally, amino acid sequences of the HAS 1, HAS 2 and HAS 3 encoded by the cDNA molecules are respectively shown in SEQ ID NO:2, SEQ ID NO:4 and SEQ ID NO:6.

By the lipofection process, the COS-7 cell was transfected with pEXneo-HAS1, pEXneo-HAS2 or pEXneo-HAS3 or a vector control (pEXneo). After 24 hours thereof, the cells were transferred into the fresh medium to allow a dilution ratio to be 1:10, and selection was carried out at 37° C. in DMEM containing 10% FCS, 2 mM L-glutamine and 0.5 mg/mL G 418. The cells survived during the selection period were cloned and used in the following test.

(1-5) Growth Inhibition Test (1-5-1) Analysis of the Activity of Inhibiting *Candida* Growth of HA Co-culture of HA and *Candida* was carried out in 100 µl of a medium using a 96 well plate (manufactured by Iwaki).

*Candida albicans* was prepared by growing it at 37° C. overnight in the GP broth under an aerobic condition. The *Candida albicans* culture mixture was incubated at 37° C. for 9 hours under a condition of 10% $CO_2$ in the presence of various final concentrations (0.1 mg/mL, 1.0 mg/mL) of HA having various sizes (tetradecasaccharide, weight average molecular weight 60 kDa, 250 kDa, 800 kDa or 2,000 kDa).

Additionally, other *Candida* species (*Candida glabrata* ATCC 2001, *Candida krusei* ATCC 6258 and *Candida tropicalis* ATCC 4563) were prepared by allowing them to grow at 37° C. overnight in the GP broth under an aerobic condition. Culture mixtures of these *Candida* species (cell density: $5 \times 10^5$) were incubated at 37° C. for 9 hours under a condition of 10% $CO_2$ together with various final concentrations (0.1 mg/mL, 1.0 mg/mL) of HA having a weight average molecular weight of 2,000 kDa.

After completion of the incubation, in order to evaluate the degree of growth of each *Candida* species, the culture medium was thoroughly mixed, and its absorbance at a wavelength of 660 nm was measured. Hereinafter, absorbance of the sample incubated in the presence of HA is referred to as "ODtest". As a control, the absorbance at a wavelength of 660 nm was measured using a sample of each *Candida* species incubated in the same manner in the absence of HA. Hereinafter, absorbance of this control is referred to as "ODcontrol".

Growth inhibition ratio (%) was calculated from the value of "ODtest" and the value of "ODcontrol" of its corresponding *Candida* species based on the following formula.

$$\text{Growth inhibition ratio (\%)} = (1 - \text{ODtest}/\text{ODcontrol}) \times 100$$

(1-5-2) Quantitative Plate Count

In order to monitor growth inhibition of *Candida albicans*, a quantitative plate count method was used (J. Infect. Dis., 182, p. 1479-1485 (2000), Infect. Immun., 69, p. 7091-7099 (2001), Med. Mycol., 37, p. 251-259 (1999)). In briefly describing, a co-culture mixture of the same effector and target was incubated at 37° C. for 9 hours under a condition of 5% $CO_2$. Thereafter, 100 µl of 0.3% Triton X-100 was added to each well in order to remove the *Candida* species, and the sample was continuously diluted ($1:10^3$) and plated on the Sabouraud-dextrin agar medium. It was incubated at 30° C. for 48 hours, and the colony forming unit (to be referred to as "CFU" hereinafter) was counted. Hereinafter, counted value of CFU of the sample incubated in the presence of HA is referred to as "test CFU".

As a control, respective *Candida* species was incubated in the absence of HA, and this was subjected to the plating in the same manner. Hereinafter, counted value of CFU on the sample is referred to as "control CFU".

Growth inhibition ratio (%) was calculated from the value of "test CFU" and the value of "control CFU" of its corresponding *Candida* species based on the following formula.

$$\text{Growth inhibition ratio (\%)} = (1 - \text{test CFU}/\text{control CFU}) \times 100$$

(1-6) Living Body Staining of *Candida* Species

Co-culturing of an epithelial cell with a *Candida* species (effector:target ratio (to be referred to as "E:T" hereinafter) is 20:1, 40:1 or 80:1) was carried out in 100 µl of a medium using a 96 well plate (manufactured by Costar). After 9 hours of incubation, the co-culture mixture was recovered and washed twice. Fluorescein diacetate (which stain living cells, to be referred to as "FDA" hereinafter) (50 µg/mL) and propidium iodide (which stain dead cells, to be referred to as "PI" hereinafter)(1 µg/mL) (both manufactured by Sigma) (Adv. Biochem. Eng. Biotechnol., 62, p. 33-73 (1998), Anal. Chem., 37, p. 1219-1221 (1965)) were simultaneously added to the pellet of cells and incubated at room temperature for 20 minutes in the dark. In this connection, optimum concentrations of the respective pigments were determined by a preliminary test.

After the incubation, the co-culture mixture was washed with PBS and then with PBS containing 20% FCS, respectively, and then again washed with PBS. The pellet was resuspended in 100 µl, of PBS, and a 5 µL thereof was put on a slide glass and observed under a fluorescent phase contrast microscope (DP-70 manufactured by Olympus Corporation). Growth inhibition of *Candida* species by the epithelial cell was confirmed by 9 hours of a growth inhibition assay.

(1-7) MTT Assay

Assay of living cells was carried out in the same manner as in the reported reference (Infect. Immun., 69, p. 5925-5930 (2001)).

In briefly describing, firstly, the COS-7 and KB cells were plated on a 96 well plate at a density of $5 \times 10^5$ cells/mL. Hyaluronidase (manufactured by Sigma) having a respective concentration of 10, 20 or 100 units/mL was added to it, and *Candida albicans* was cultured for 20 hours. MTT solution (20 µg/mL) was added to each well at the final stage of the culturing, and the contents of the plate were incubated for 4 hours. By adding 100 µL of acidic isopropanol (isopropanol containing 0.04M HCl) to this, the red formazan was eluted and thoroughly mixed. Formazan concentration in the solution of each well was measured by a plate reader (manufactured by Dynex) using 570 nm as the testing wavelength and 620 nm as the reference wave length, respectively.

(1-8) Measurement of HA Concentration by Competitive ELISA-like Assay

A culture mixture of exponentially proliferating cells and a culture mixture of cells which reached confluent state were cultured for 24 hours using a fresh medium, and the conditioned medium was recovered. The HA concentration in this conditioned medium was measured by the already reported competitive ELISA-like assay (J. Biol. Chem., 274, p. 25085-25092 (1999)).

In briefly describing, the recovered conditioned medium was mixed with a biotin-labeled HA binding protein (manufactured by Seikagaku Corporation) and incubated at 4° C. for 20 hours. This mixture was added to a 96 well plate to which HA was bound and incubated at room temperature for 6 hours. The alkaline phosphatase activity was measured using alkaline phosphatase-linked streptavidin as the secondary prove and p-nitrophenyl phosphate as the substrate, respectively. The HA concentration was calculated using a calibration curve.

(1-9) Statistical Analysis

All of the data are shown as average value±standard deviation (to be referred to as "SD" hereinafter). The significance test was carried out by the unpaired Student's t test. In the case of $p<0.05$, the result was regarded as statistically significant. All of the statistic treatments were carried out using SPSS11.0J (manufactured by SPSS Japan)

(2) Results (2-1) Growth Inhibition of *Candida* by Epithelial Cell

In order to examine whether or not the epithelial cells (KB cell and GE 1 cell) have activity of inhibiting the *Candida* growth, growth inhibition ratio of *Candida albicans* was measured and calculated by the quantitative plate count, and the average value±SD of three tests was calculated. The results are shown in FIG. 1.

From FIG. 1, it was shown that both cells have the activity of inhibiting *Candida* growth.

(2-2) *Candida* Growth Inhibition by HA on the Cell Surface

In order to examine the role of extracellular HA, an epithelial cell (KB cell) and a fibroblast (COS-7 cell) from which HA on the cell surface was removed by treating with various concentrations of hyaluronidase were used and growth inhibition ratio of *Candida albicans* was measured and calculated in the same manner as in the aforementioned (2-1). The average value±SD of three tests was calculated. In this case, the ratio was set to E:T±80:1. The results are shown in FIG. 2.

Figure 2:
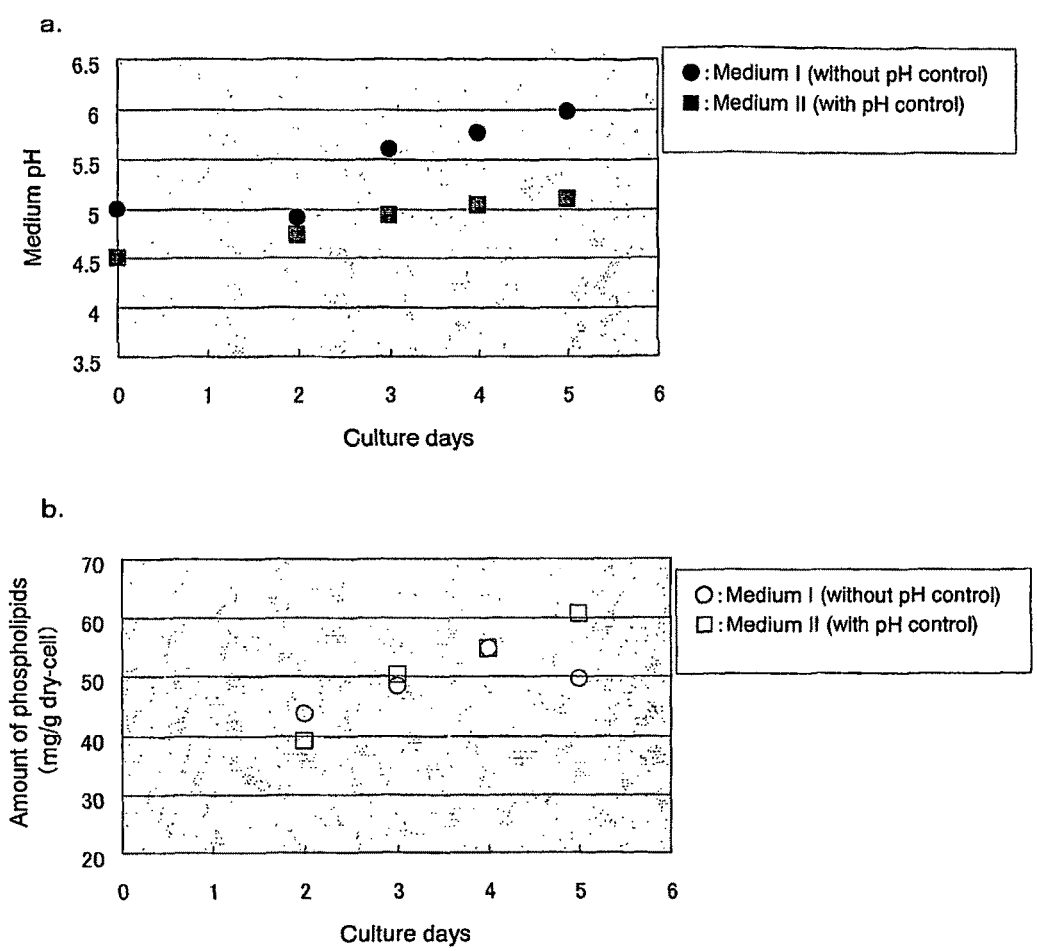
FIG. 2 is a graph showing activity of inhibiting *Candida* growth by HA on the cell surface.

From FIG. 2, it was shown that the activity of inhibiting *Candida* growth of the KB cell and COS-7 cell is reduced by the treatment of the cells with hyaluronidase. In this connection, it was shown by the MTT assay that the hyaluronidase treatment does not exert influence upon the life or death of the cells (data not shown).

(2-3) *Candida* Growth Inhibition by HA

In order to examine whether or not HA has the activity of inhibiting *Candida* growth, *Candida albicans* ($5 \times 10^5$ (cells/mL)) was incubated for 9 hours together with HA of various levels of concentration and weight average molecular weight, and growth inhibition ratio of *Candida albicans* was measured and calculated. The average value±SD of three tests was calculated. The results are shown in FIG. 3.

Figure 3:
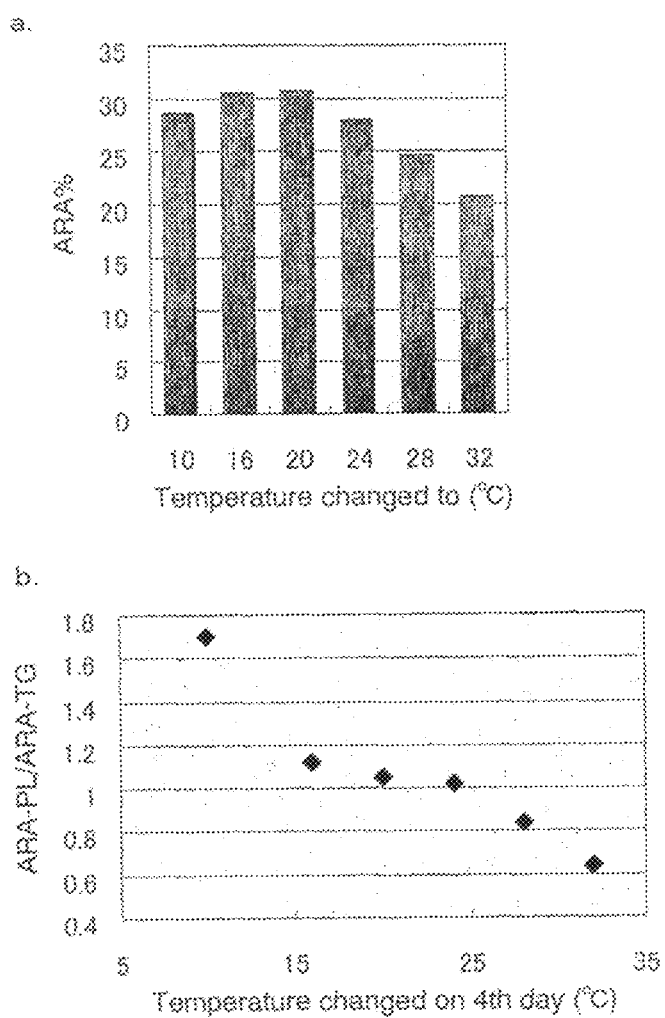
FIG. 3 is a graph showing activity of inhibiting *Candida* growth by HA.

From FIG. 3, it was shown that HA has activity of inhibiting the *Candida albicans* growth. Additionally, it was shown that the activity is significant in high molecular weight HA and is significant in high concentration HA.

(2-4) Reinforcement of the Activity of Inhibiting *Candida* Growth of a Cell by the Transfection of HAS Gene COS-7 cell was transfected with three kinds of pEXneo-HAS or pEXneo (control) and incubated for 9 hours together with *Candida albicans*. The amounts of HA produced from a constant density of the cell ($1 \times 10^6$ cells/mL) are shown below.

pEX-HAS 1: 453.9 ng/mL
pEX-HAS 2: 494.0 ng/mL
pEX-HAS 3: 347.0 ng/mL
pEXneo: 75.4 ng/mL It was shown from the result that each of the three kinds of HAS transfectants produces extracellular HA at a high level in comparison with pEXneo.

Figure 4:
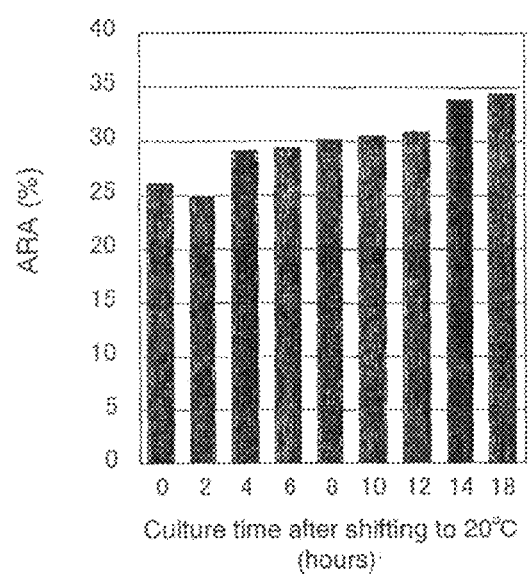
FIG. 4 is a graph showing the reinforced activity of a cell of inhibiting *Candida* growth by the transfection of HAS gene.

Additionally, using the COS-7 cells transfected with these vectors, growth inhibition ratio of *Candida albicans* was measured and calculated in the same manner as in the aforementioned (2-1). The average value±SD of three tests was calculated. In this case, the ratio was set to E:T=80:1. The results are shown in FIG. 4. In this connection, the asterisk in FIG. 4 shows that it has a significant difference against the control.

It was shown from FIG. 4 that the cells transfected with each HAS have a significantly high activity of inhibiting *Candida* growth in comparison with the control.

(2-5) Bacteriostatic or Bactericidal Activity of KB Cell

In order to examine whether the *Candida* growth inhibition by KB cell is due to the sterilization of *Candida albicans* or the delay of its growth, PI and FDA were added to the cells derived from a co-culture mixture of epithelial cell and *Candida albicans* (E:T=10:1). *Candida albicans* cultured in the absence of KB cell was used as the control.

As a result, the KB cell did not sterilize *Candida albicans*. The result was the same in the case of E:T=80:1.

It was shown that *Candida albicans* survived by the living body staining even after 9 hours of incubation using a medium containing 2,000 kDa of HA. Additionally, it was shown by fluorescence microscopic images of the 9 hour co-culture mixture of KB cell and *Candida albicans* that the HAS 1 transfectant does not sterilize *Candida albicans* and that survived *Candida albicans* is present in the culture medium. The result was the same also in the case of HAS 2 and HAS 3 transfectants.

Based on these results, it was shown that the activity of inhibiting *Candida* growth possessed by HA is not bactericidal but rather bacteriostatic.

(2-6) Activity of Inhibiting Growth for Various *Candida* Species by HA

In order to examine whether or not HA exerts activity of inhibiting growth also for other *Candida* species than *Candida albicans*, other *Candida* species ($5 \times 10^5$ (cells/mL)) were incubated at room temperature for 9 hours together with an HA of 2,000 kDa, and growth inhibition ratio of *Candida albicans* was measured and calculated. The average value±SD of three tests was calculated. The results are shown in FIG. 5.

Figure 5:
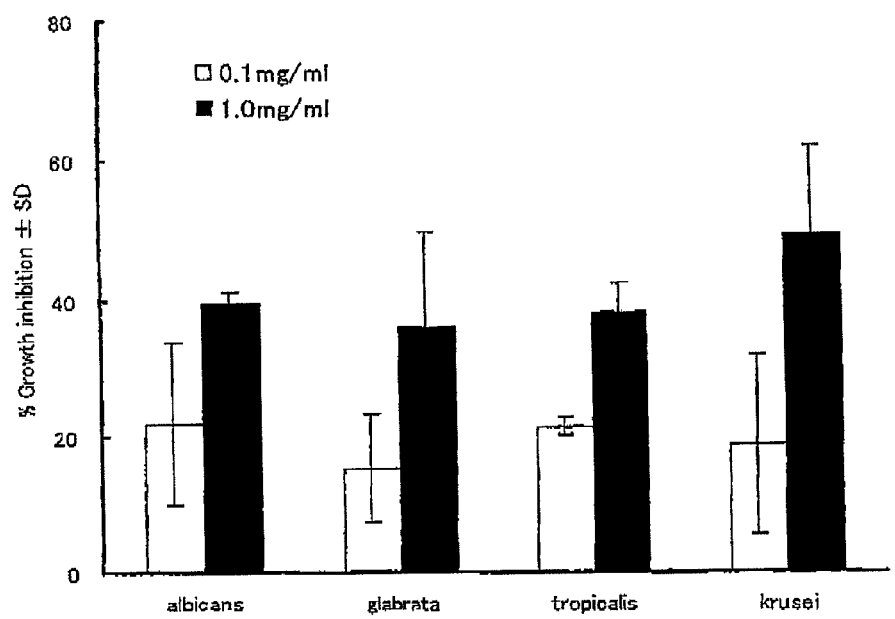
FIG. 5 is a graph showing the activity of HA of inhibiting growth of various *Candida* species.

From FIG. 5, it was shown that HA exerts its activity of inhibiting growth not only for *Candida albicans* but also for other various *Candida* species.

Based on the above results, it was shown that HA has a considerable ability of inhibiting growth for fungi. Additionally, it was shown that the ability of inhibiting growth for fungi is reinforced in the cell transfected with a cDNA encoding HAS.

Based on this, it was shown that HA is useful as the active ingredient of a fungal growth inhibitor, that a cDNA encoding HAS is useful for reinforcing activity of inhibiting fungal growth of a cell and that a cell transfected with a cDNA encoding HAS is useful as a fungal growth inhibitor.

While the present invention has been described in detail and with reference to specific embodiments thereof, it will be apparent to one skilled in the art that various changes and modifications can be made therein without departing from the spirit and scope of the present invention.

This application is based on a Japanese patent application filed on Feb. 10, 2006 (Japanese Patent Application No. 2006-033418), and the entire contents thereof is incorporated by reference. All references cited herein are incorporated as a whole.

Industrial Applicability

The inhibitor of the present invention and inhibition method 1 of the present invention are markedly useful, since they can significantly inhibit growth of fungi and the safety of their active ingredient (HA or a salt thereof) is also markedly high. Also, the reinforcing agent and reinforcing method of the present invention are markedly useful, since they can strongly reinforce the activity of inhibiting fungal growth possessed by a cell. In addition, the inhibition method 2 of the present invention is markedly useful, because fungal growth can be significantly inhibited by applying the reinforcing agent and reinforcing method of the present invention.

The invention claimed is:

1. A method for inhibiting fungal growth in cell culture, comprising culturing a cell transfected with a DNA encoding a hyaluronic acid synthase in a culture medium, under conditions permissive for fungal growth, in the presence of a fungus;
wherein the growth of said fungus during said culturing is reduced in comparison to the growth of said fungus under said conditions when said cell is not transfected with said DNA;
wherein the concentration of hyaluronic acid in said culture medium during said culturing reaches at least 347 ng/ml;
and wherein said fungus is from the genus *Candida*.

2. The method of claim 1, wherein the hyaluronic acid synthase is at least one hyaluronic acid synthase selected from the group consisting of hyaluronic acid synthase 1, hyaluronic acid synthase 2, and hyaluronic acid synthase 3.

3. The method of claim 2, wherein the at least one hyaluronic acid synthase is hyaluronic acid synthase 1.

4. The method of claim 2, wherein the at least one hyaluronic acid synthase is hyaluronic acid synthase 2.

5. The method of claim 2, wherein the at least one hyaluronic acid synthase is hyaluronic acid synthase 3.

6. The method of claim 1, wherein the cell is an epithelial cell or a fibroblast.

* * * * *

SEQUENCE LISTING

<160> NUMBER OF SEQ ID NOS: 6

<210> SEQ ID NO 1
<211> LENGTH: 1752
<212> TYPE: DNA
<213> ORGANISM: Mus musculus
<220> FEATURE:
<221> NAME/KEY: CDS
<222> LOCATION: (1)..(1752)

<400> SEQUENCE: 1

```
atg aga cag gac atg cca aag ccc tca gag gca gcg cgt tgc tgc tct      48
Met Arg Gln Asp Met Pro Lys Pro Ser Glu Ala Ala Arg Cys Cys Ser
1               5                   10                  15 ggc ctg gcc agg cga gca ctc acg atc atc ttt gcc ctg ctc atc ctg      96
Gly Leu Ala Arg Arg Ala Leu Thr Ile Ile Phe Ala Leu Leu Ile Leu
                20                  25                  30 ggc ctc atg acc tgg gcc tac gcc gca ggc gtt cct ctg gct tca gat     144
Gly Leu Met Thr Trp Ala Tyr Ala Ala Gly Val Pro Leu Ala Ser Asp
            35                  40                  45 cgc tat gga ctc ctg gcc ttt ggc ctc tat ggg gca ttc ctc agc gca     192
Arg Tyr Gly Leu Leu Ala Phe Gly Leu Tyr Gly Ala Phe Leu Ser Ala
        50                  55                  60 cac cta gtg gca cag agc ctc ttc gct tac ctg gag cac cga agg gtg     240
His Leu Val Ala Gln Ser Leu Phe Ala Tyr Leu Glu His Arg Arg Val
65                  70                  75                  80 gca gcg gct gcg cgg cgc tcc ttg gcg aag ggg ccc ctg gat gcg gcc     288
Ala Ala Ala Ala Arg Arg Ser Leu Ala Lys Gly Pro Leu Asp Ala Ala
                85                  90                  95 act gca cgc agc gtg gca ctc acc atc tca gcc tac caa gag gat ccc     336
Thr Ala Arg Ser Val Ala Leu Thr Ile Ser Ala Tyr Gln Glu Asp Pro
                100                 105                 110 gct tac ctg cgc cag tgc ttg acc tcc gcg cgc gcc ttg ctg tac ccg     384
Ala Tyr Leu Arg Gln Cys Leu Thr Ser Ala Arg Ala Leu Leu Tyr Pro
            115                 120                 125 cac acg agg tta cgc gtg ctc atg gtg gtg gac ggc aac cgc gct gag     432
His Thr Arg Leu Arg Val Leu Met Val Val Asp Gly Asn Arg Ala Glu
        130                 135                 140 gat ctg tac atg gtg gac atg ttc cga gaa gtc ttc gcc gat gag gac     480
Asp Leu Tyr Met Val Asp Met Phe Arg Glu Val Phe Ala Asp Glu Asp
145                 150                 155                 160 ccc gcc act tat gtg tgg gat ggc aac tac cat cag ccc tgg gaa cca     528
Pro Ala Thr Tyr Val Trp Asp Gly Asn Tyr His Gln Pro Trp Glu Pro
                165                 170                 175 gcg gag gct acg ggc gct gtc ggt gaa ggt gcc tac cgg gag gtg gag     576
Ala Glu Ala Thr Gly Ala Val Gly Glu Gly Ala Tyr Arg Glu Val Glu
            180                 185                 190 gcg gag gac ccc ggg cgg ttg gcg gtg gag gcg ctg gtg aga aca cgc     624
Ala Glu Asp Pro Gly Arg Leu Ala Val Glu Ala Leu Val Arg Thr Arg
        195                 200                 205 agg tgc gtg tgc gtg gct cag cgt tgg ggc ggc aaa cgt gag gtc atg     672
Arg Cys Val Cys Val Ala Gln Arg Trp Gly Gly Lys Arg Glu Val Met
    210                 215                 220 tac aca gct ttc aag gca ctg ggc gac tcc gtg gac tac gtg cag gtc     720
Tyr Thr Ala Phe Lys Ala Leu Gly Asp Ser Val Asp Tyr Val Gln Val
225                 230                 235                 240 tgt gac tca gac aca aga cta gac ccc atg gca ctg ctg gag ctt gtg     768
Cys Asp Ser Asp Thr Arg Leu Asp Pro Met Ala Leu Leu Glu Leu Val
                245                 250                 255 cga gtg ttg gat gaa gac ccc cgg gta ggg gct gtt gga ggg gat gtg     816
```

```
                    Arg Val Leu Asp Glu Asp Pro Arg Val Gly Ala Val Gly Gly Asp Val
                                    260                 265                 270 agg atc ctt aac cct ctg gac tcc tgg gtc agc ttc ttg agc agt ctt           864
Arg Ile Leu Asn Pro Leu Asp Ser Trp Val Ser Phe Leu Ser Ser Leu
            275                 280                 285 cga tac tgg gta gcc ttc aat gtg gaa cga gct tgt cag agc tac ttc           912
Arg Tyr Trp Val Ala Phe Asn Val Glu Arg Ala Cys Gln Ser Tyr Phe
        290                 295                 300 cac tgt gtg tcc tgc atc agt ggt cct ctg ggt cta tac aga aac aat           960
His Cys Val Ser Cys Ile Ser Gly Pro Leu Gly Leu Tyr Arg Asn Asn
305                 310                 315                 320 ctc ctg cag cag ttc ttg gag gcc tgg tac aac caa aag ttc ctg ggc          1008
Leu Leu Gln Gln Phe Leu Glu Ala Trp Tyr Asn Gln Lys Phe Leu Gly
                325                 330                 335 acc cac tgc aca ttt ggg gat gac agg cac ctc acc aac cga atg ctt          1056
Thr His Cys Thr Phe Gly Asp Asp Arg His Leu Thr Asn Arg Met Leu
            340                 345                 350 agc atg ggc tat gct acc aag tat acc tcg cgc tcc aga tgc tac tcg          1104
Ser Met Gly Tyr Ala Thr Lys Tyr Thr Ser Arg Ser Arg Cys Tyr Ser
        355                 360                 365 gag acg ccc tcc tcc ttc ctt cgt tgg ttg agc caa cag acc cgc tgg          1152
Glu Thr Pro Ser Ser Phe Leu Arg Trp Leu Ser Gln Gln Thr Arg Trp
370                 375                 380 tcc aaa tct tac ttc cga gag tgg cta tac aat gct ctg tgg tgg cat          1200
Ser Lys Ser Tyr Phe Arg Glu Trp Leu Tyr Asn Ala Leu Trp Trp His
385                 390                 395                 400 cgc cac cac gca tgg atg acc tat gaa gcg gtg gtc tcg ggc ctc ttc          1248
Arg His His Ala Trp Met Thr Tyr Glu Ala Val Val Ser Gly Leu Phe
                405                 410                 415 cct ttc ttc gtg gct gcc acg gtg ttg agg ctc ttc tat gca ggg cgc          1296
Pro Phe Phe Val Ala Ala Thr Val Leu Arg Leu Phe Tyr Ala Gly Arg
            420                 425                 430 ccg tgg gct ctg ctc tgg gtg ctg ctc tgt gtg cag ggc gta gca ctg          1344
Pro Trp Ala Leu Leu Trp Val Leu Leu Cys Val Gln Gly Val Ala Leu
        435                 440                 445 gca aag gca gcc ttt gca gcc tgg ctg cgt ggc tgc gtg cgc atg gtg          1392
Ala Lys Ala Ala Phe Ala Ala Trp Leu Arg Gly Cys Val Arg Met Val
450                 455                 460 ctg ctg tca ctc tat gca cca ctc tac atg tgc ggc ctc ctg cct gcc          1440
Leu Leu Ser Leu Tyr Ala Pro Leu Tyr Met Cys Gly Leu Leu Pro Ala
465                 470                 475                 480 aaa ttc cta gcg ttg gtt acc atg aat caa agt ggt tgg ggt acc tcg          1488
Lys Phe Leu Ala Leu Val Thr Met Asn Gln Ser Gly Trp Gly Thr Ser
                485                 490                 495 ggc cgg aag aaa ctg gct gct aac tat gtc ccc gtg ttg ccc ctg gca          1536
Gly Arg Lys Lys Leu Ala Ala Asn Tyr Val Pro Val Leu Pro Leu Ala
            500                 505                 510 ctc tgg gct cta ctg ctg ctt gga ggc ctg gcc cgc agt gtg gcc cag          1584
Leu Trp Ala Leu Leu Leu Leu Gly Gly Leu Ala Arg Ser Val Ala Gln
        515                 520                 525 gag gcc aga gct gac tgg agt ggc cca tcc cga gca gct gaa gcc tac          1632
Glu Ala Arg Ala Asp Trp Ser Gly Pro Ser Arg Ala Ala Glu Ala Tyr
530                 535                 540 cac ctt gct gct ggg gct ggt gcc tat gtg gcc tac tgg gtg gta atg          1680
His Leu Ala Ala Gly Ala Gly Ala Tyr Val Ala Tyr Trp Val Val Met
545                 550                 555                 560 tta act atc tac tgg gta ggt gtg agg agg ctg tgc aga cgt cgg agc          1728
Leu Thr Ile Tyr Trp Val Gly Val Arg Arg Leu Cys Arg Arg Arg Ser
                565                 570                 575 ggt ggt tac cgt gtc caa gta tga                                          1752
```

Gly Gly Tyr Arg Val Gln Val
            580

<210> SEQ ID NO 2
<211> LENGTH: 583
<212> TYPE: PRT
<213> ORGANISM: Mus musculus

<400> SEQUENCE: 2

Met Arg Gln Asp Met Pro Lys Pro Ser Glu Ala Arg Cys Cys Ser
1               5                   10                  15

Gly Leu Ala Arg Arg Ala Leu Thr Ile Ile Phe Ala Leu Leu Ile Leu
            20                  25                  30

Gly Leu Met Thr Trp Ala Tyr Ala Ala Gly Val Pro Leu Ala Ser Asp
            35                  40                  45

Arg Tyr Gly Leu Leu Ala Phe Gly Leu Tyr Gly Ala Phe Leu Ser Ala
            50                  55                  60

His Leu Val Ala Gln Ser Leu Phe Ala Tyr Leu Glu His Arg Arg Val
65                  70                  75                  80

Ala Ala Ala Ala Arg Arg Ser Leu Ala Lys Gly Pro Leu Asp Ala Ala
                85                  90                  95

Thr Ala Arg Ser Val Ala Leu Thr Ile Ser Ala Tyr Gln Glu Asp Pro
            100                 105                 110

Ala Tyr Leu Arg Gln Cys Leu Thr Ser Ala Arg Ala Leu Leu Tyr Pro
            115                 120                 125

His Thr Arg Leu Arg Val Leu Met Val Val Asp Gly Asn Arg Ala Glu
            130                 135                 140

Asp Leu Tyr Met Val Asp Met Phe Arg Glu Val Phe Ala Asp Glu Asp
145                 150                 155                 160

Pro Ala Thr Tyr Val Trp Asp Gly Asn Tyr His Gln Pro Trp Glu Pro
                165                 170                 175

Ala Glu Ala Thr Gly Ala Val Gly Glu Gly Ala Tyr Arg Glu Val Glu
            180                 185                 190

Ala Glu Asp Pro Gly Arg Leu Ala Val Glu Ala Leu Val Arg Thr Arg
            195                 200                 205

Arg Cys Val Cys Val Ala Gln Arg Trp Gly Gly Lys Arg Glu Val Met
            210                 215                 220

Tyr Thr Ala Phe Lys Ala Leu Gly Asp Ser Val Asp Tyr Val Gln Val
225                 230                 235                 240

Cys Asp Ser Asp Thr Arg Leu Asp Pro Met Ala Leu Leu Glu Leu Val
                245                 250                 255

Arg Val Leu Asp Glu Asp Pro Arg Val Gly Ala Val Gly Gly Asp Val
            260                 265                 270

Arg Ile Leu Asn Pro Leu Asp Ser Trp Val Ser Phe Leu Ser Ser Leu
            275                 280                 285

Arg Tyr Trp Val Ala Phe Asn Val Glu Arg Ala Cys Gln Ser Tyr Phe
            290                 295                 300

His Cys Val Ser Cys Ile Ser Gly Pro Leu Gly Leu Tyr Arg Asn Asn
305                 310                 315                 320

Leu Leu Gln Gln Phe Leu Glu Ala Trp Tyr Asn Gln Lys Phe Leu Gly
                325                 330                 335

Thr His Cys Thr Phe Gly Asp Asp Arg His Leu Thr Asn Arg Met Leu
            340                 345                 350

Ser Met Gly Tyr Ala Thr Lys Tyr Thr Ser Arg Ser Arg Cys Tyr Ser
            355                 360                 365

```
Glu Thr Pro Ser Ser Phe Leu Arg Trp Leu Ser Gln Gln Thr Arg Trp
    370                 375                 380

Ser Lys Ser Tyr Phe Arg Glu Trp Leu Tyr Asn Ala Leu Trp Trp His
385                 390                 395                 400

Arg His His Ala Trp Met Thr Tyr Glu Ala Val Val Ser Gly Leu Phe
                405                 410                 415

Pro Phe Phe Val Ala Ala Thr Val Leu Arg Leu Phe Tyr Ala Gly Arg
            420                 425                 430

Pro Trp Ala Leu Leu Trp Val Leu Cys Val Gln Gly Val Ala Leu
        435                 440                 445

Ala Lys Ala Ala Phe Ala Ala Trp Leu Arg Gly Cys Val Arg Met Val
    450                 455                 460

Leu Leu Ser Leu Tyr Ala Pro Leu Tyr Met Cys Gly Leu Leu Pro Ala
465                 470                 475                 480

Lys Phe Leu Ala Leu Val Thr Met Asn Gln Ser Gly Trp Gly Thr Ser
                485                 490                 495

Gly Arg Lys Lys Leu Ala Ala Asn Tyr Val Pro Val Leu Pro Leu Ala
            500                 505                 510

Leu Trp Ala Leu Leu Leu Gly Gly Leu Ala Arg Ser Val Ala Gln
        515                 520                 525

Glu Ala Arg Ala Asp Trp Ser Gly Pro Ser Arg Ala Ala Glu Ala Tyr
    530                 535                 540

His Leu Ala Ala Gly Ala Gly Ala Tyr Val Ala Tyr Trp Val Val Met
545                 550                 555                 560

Leu Thr Ile Tyr Trp Val Gly Val Arg Arg Leu Cys Arg Arg Ser
                565                 570                 575

Gly Gly Tyr Arg Val Gln Val
            580

<210> SEQ ID NO 3
<211> LENGTH: 1659
<212> TYPE: DNA
<213> ORGANISM: Mus musculus
<220> FEATURE:
<221> NAME/KEY: CDS
<222> LOCATION: (1)..(1659)

<400> SEQUENCE: 3 atg cat tgt gag agg ttt cta tgt gtc ctg aga ata att gga act aca    48
Met His Cys Glu Arg Phe Leu Cys Val Leu Arg Ile Ile Gly Thr Thr
1               5                   10                  15 ctt ttt gga gtg tct ctc ctc ctc gga atc aca gct gct tat att gtt    96
Leu Phe Gly Val Ser Leu Leu Leu Gly Ile Thr Ala Ala Tyr Ile Val
                20                  25                  30 ggc tac cag ttt atc caa aca gat aat tac tac ttc tca ttt gga ctg   144
Gly Tyr Gln Phe Ile Gln Thr Asp Asn Tyr Tyr Phe Ser Phe Gly Leu
            35                  40                  45 tac ggt gcc ttt tta gcc tcg cat ctc atc atc caa agc ctc ttt gcc   192
Tyr Gly Ala Phe Leu Ala Ser His Leu Ile Ile Gln Ser Leu Phe Ala
        50                  55                  60 ttt ttg gaa cac cgg aaa atg aag aag tcc ctt gaa acc ccg att aaa   240
Phe Leu Glu His Arg Lys Met Lys Lys Ser Leu Glu Thr Pro Ile Lys
65                  70                  75                  80 ttg aac aaa acg gta gca ctc tgc atc gct gcg tac caa gag gac cct   288
Leu Asn Lys Thr Val Ala Leu Cys Ile Ala Ala Tyr Gln Glu Asp Pro
                85                  90                  95 gac tac tta cgg aaa tgt ttg caa tct gtg aaa agg ctg acc tac cct   336
Asp Tyr Leu Arg Lys Cys Leu Gln Ser Val Lys Arg Leu Thr Tyr Pro
            100                 105                 110
```

```
ggg att aaa gtc gtg atg gtc atc gat ggg aac tca gac gac gac ctt        384
Gly Ile Lys Val Val Met Val Ile Asp Gly Asn Ser Asp Asp Asp Leu
        115                 120                 125 tac atg atg gac ata ttc agc gaa gtt att ggc agg gac aaa tcg gcc        432
Tyr Met Met Asp Ile Phe Ser Glu Val Ile Gly Arg Asp Lys Ser Ala
130                 135                 140 acg tac atc tgg aag aac aac ttt cat gaa aag gga cct ggt gag aca        480
Thr Tyr Ile Trp Lys Asn Asn Phe His Glu Lys Gly Pro Gly Glu Thr
145                 150                 155                 160 gaa gag tcc cat aaa gaa agt tca caa cat gtc acc caa ttg gtc ttg        528
Glu Glu Ser His Lys Glu Ser Ser Gln His Val Thr Gln Leu Val Leu
                165                 170                 175 tct aac aaa agt att tgc atc atg caa aaa tgg ggt gga aag aga gaa        576
Ser Asn Lys Ser Ile Cys Ile Met Gln Lys Trp Gly Gly Lys Arg Glu
            180                 185                 190 gtc atg tac aca gcc ttc aga gca ctg ggg cga agc gtg gat tat gta        624
Val Met Tyr Thr Ala Phe Arg Ala Leu Gly Arg Ser Val Asp Tyr Val
        195                 200                 205 cag gtg tgt gac tca gat act atg ctt gac cct gcc tca tct gtg gag        672
Gln Val Cys Asp Ser Asp Thr Met Leu Asp Pro Ala Ser Ser Val Glu
    210                 215                 220 atg gtg aag gtc tta gag gaa gac cct atg gtt gga ggt gtt gga gga        720
Met Val Lys Val Leu Glu Glu Asp Pro Met Val Gly Gly Val Gly Gly
225                 230                 235                 240 gat gtc cag att tta aac aag tat gat tcc tgg atc tcc ttc ctc agc        768
Asp Val Gln Ile Leu Asn Lys Tyr Asp Ser Trp Ile Ser Phe Leu Ser
                245                 250                 255 agc gtg aga tac tgg atg gct ttt aat ata gaa agg gcc tgc cag tct        816
Ser Val Arg Tyr Trp Met Ala Phe Asn Ile Glu Arg Ala Cys Gln Ser
            260                 265                 270 tat ttt ggc tgt gtc cag tgc ata agc ggt cct ctg gga atg tac aga        864
Tyr Phe Gly Cys Val Gln Cys Ile Ser Gly Pro Leu Gly Met Tyr Arg
        275                 280                 285 aac tcc ttg ctg cat gaa ttt gtg gaa gac tgg tac aat cag gaa ttc        912
Asn Ser Leu Leu His Glu Phe Val Glu Asp Trp Tyr Asn Gln Glu Phe
    290                 295                 300 atg ggt aac caa tgc agt ttt ggt gac gac agg cac ctt acc aac agg        960
Met Gly Asn Gln Cys Ser Phe Gly Asp Asp Arg His Leu Thr Asn Arg
305                 310                 315                 320 gtg ttg agt ctg ggc tat gca act aaa tac acg gct cgg tcc aag tgc        1008
Val Leu Ser Leu Gly Tyr Ala Thr Lys Tyr Thr Ala Arg Ser Lys Cys
                325                 330                 335 ctt act gaa act ccc ata gaa tat ctg aga tgg ctg aac cag cag acc        1056
Leu Thr Glu Thr Pro Ile Glu Tyr Leu Arg Trp Leu Asn Gln Gln Thr
            340                 345                 350 cga tgg agc aag tcc tac ttc cga gag tgg ctg tac aat gcc atg tgg        1104
Arg Trp Ser Lys Ser Tyr Phe Arg Glu Trp Leu Tyr Asn Ala Met Trp
        355                 360                 365 ttt cac aag cat cac ctg tgg atg acc tat gaa gct gtt atc act gga        1152
Phe His Lys His His Leu Trp Met Thr Tyr Glu Ala Val Ile Thr Gly
    370                 375                 380 ttc ttt cct ttc ttt ctc att gcc aca gtc atc cag ctc ttc tac agg        1200
Phe Phe Pro Phe Phe Leu Ile Ala Thr Val Ile Gln Leu Phe Tyr Arg
385                 390                 395                 400 ggt aaa atc tgg aac atc ctc ctc ttc ctg tta act gtc cag cta gtg        1248
Gly Lys Ile Trp Asn Ile Leu Leu Phe Leu Leu Thr Val Gln Leu Val
                405                 410                 415 ggt ctc atc aag tca tct ttt gcc agc tgc ctt aga gga aat atc gtc        1296
Gly Leu Ile Lys Ser Ser Phe Ala Ser Cys Leu Arg Gly Asn Ile Val
            420                 425                 430
```

-continued

```
atg gta ttc atg tct ctg tat tca gtg tta tac atg tca agt cta ctt    1344
Met Val Phe Met Ser Leu Tyr Ser Val Leu Tyr Met Ser Ser Leu Leu
    435                 440                 445 cct gcc aag atg ttt gca att gca acc ata aac aaa gct ggg tgg ggc    1392
Pro Ala Lys Met Phe Ala Ile Ala Thr Ile Asn Lys Ala Gly Trp Gly
450                 455                 460 aca tct gga agg aag acc att gtt gtt aat ttc ata gga ctt att cca    1440
Thr Ser Gly Arg Lys Thr Ile Val Val Asn Phe Ile Gly Leu Ile Pro
465                 470                 475                 480 gtg tcc gtg tgg ttt aca atc ctt cta ggt ggt gta att ttc acc att    1488
Val Ser Val Trp Phe Thr Ile Leu Leu Gly Gly Val Ile Phe Thr Ile
                485                 490                 495 tat aag gaa tct aaa aag cca ttt tcc gaa tcc aaa cag act gtt ctc    1536
Tyr Lys Glu Ser Lys Lys Pro Phe Ser Glu Ser Lys Gln Thr Val Leu
            500                 505                 510 atc gtg gga act ttg atc tat gca tgc tac tgg gtc atg ctt ttg act    1584
Ile Val Gly Thr Leu Ile Tyr Ala Cys Tyr Trp Val Met Leu Leu Thr
        515                 520                 525 ctc tat gtg gtt ctc atc aat aag tgt ggc agg cgg aag aag gga caa    1632
Leu Tyr Val Val Leu Ile Asn Lys Cys Gly Arg Arg Lys Lys Gly Gln
530                 535                 540 cag tat gac atg gtg ctt gat gta tga                                1659
Gln Tyr Asp Met Val Leu Asp Val
545                 550
```

<210> SEQ ID NO 4
<211> LENGTH: 552
<212> TYPE: PRT
<213> ORGANISM: Mus musculus

<400> SEQUENCE: 4

```
Met His Cys Glu Arg Phe Leu Cys Val Leu Arg Ile Ile Gly Thr Thr
1               5                   10                  15

Leu Phe Gly Val Ser Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Asp Asp Leu
        115                 120                 125

Tyr Met Met Asp Ile Phe Ser Glu Val Ile Gly Arg Asp Lys Ser Ala
    130                 135                 140

Thr Tyr Ile Trp Lys Asn Asn Phe His Glu Lys Gly Pro Gly Glu Thr
145                 150                 155                 160

Glu Glu Ser His Lys Glu Ser Ser Gln His Val Thr Gln Leu Val Leu
                165                 170                 175

Ser Asn Lys Ser Ile Cys Ile Met Gln Lys Trp Gly Lys Arg Glu
            180                 185                 190

Val Met Tyr Thr Ala Phe Arg Ala Leu Gly Arg Ser Val Asp Tyr Val
        195                 200                 205
```

```
Gln Val Cys Asp Ser Asp Thr Met Leu Asp Pro Ala Ser Ser Val Glu
    210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
    290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
    370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
    450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
            500                 505                 510

Ile Val Gly Thr Leu Ile Tyr Ala Cys Tyr Trp Val Met Leu Leu Thr
        515                 520                 525

Leu Tyr Val Val Leu Ile Asn Lys Cys Gly Arg Arg Lys Lys Gly Gln
    530                 535                 540

Gln Tyr Asp Met Val Leu Asp Val
545                 550

<210> SEQ ID NO 5
<211> LENGTH: 1665
<212> TYPE: DNA
<213> ORGANISM: Mus musculus
<220> FEATURE:
<221> NAME/KEY: CDS
<222> LOCATION: (1)..(1665)

<400> SEQUENCE: 5 atg ccg gtg cag ctg act aca gcc ctg cgt gtg gtg ggc acc agt ctg      48
Met Pro Val Gln Leu Thr Thr Ala Leu Arg Val Val Gly Thr Ser Leu
1               5                   10                  15
```

| | | | | | | | | | | | | | | | |
|---|---|---|---|---|---|---|---|---|---|---|---|---|---|---|---|
| ttt | gcc | ctg | gta | gtg | ctg | gga | ggc | atc | ctg | gcg | gcc | tat | gtg | aca | ggc | 96 |
| Phe | Ala | Leu | Val | Val | Leu | Gly | Gly | Ile | Leu | Ala | Ala | Tyr | Val | Thr | Gly | |
| | | 20 | | | | 25 | | | | 30 | | | | | | |

| tac | cag | ttt | atc | cac | aca | gaa | aag | cac | tac | ctg | tcc | ttt | ggc | ctc | tac | 144 |
| Tyr | Gln | Phe | Ile | His | Thr | Glu | Lys | His | Tyr | Leu | Ser | Phe | Gly | Leu | Tyr |
| | 35 | | | | 40 | | | | | 45 | | | | | |

| ggt | gcc | atc | ctg | ggt | cta | cat | ctg | ctc | atc | cag | agc | ctg | ttt | gcc | ttc | 192 |
| Gly | Ala | Ile | Leu | Gly | Leu | His | Leu | Leu | Ile | Gln | Ser | Leu | Phe | Ala | Phe |
| 50 | | | | | 55 | | | | | 60 | | | | | |

| ctg | gag | cac | cgt | cga | atg | cgg | gca | ggg | cgc | ccc | ctc | aag | ctg | cac | | 240 |
| Leu | Glu | His | Arg | Arg | Met | Arg | Ala | Gly | Arg | Pro | Leu | Lys | Leu | His |
| 65 | | | | 70 | | | | 75 | | | | 80 | | | |

| tgc | tcc | cag | agg | tcg | cgt | tca | gtg | gca | ctc | tgc | att | gct | gcc | tac | caa | 288 |
| Cys | Ser | Gln | Arg | Ser | Arg | Ser | Val | Ala | Leu | Cys | Ile | Ala | Ala | Tyr | Gln |
| | | | 85 | | | | | 90 | | | | | 95 | | |

| gag | gac | ccc | gaa | tac | ctg | cgc | aag | tgc | ctt | cgc | tca | gct | cag | cgc | att | 336 |
| Glu | Asp | Pro | Glu | Tyr | Leu | Arg | Lys | Cys | Leu | Arg | Ser | Ala | Gln | Arg | Ile |
| | | 100 | | | | | 105 | | | | | 110 | | | |

| gcc | ttt | cca | aac | ctc | aag | gtg | gtc | atg | gta | gtg | gat | ggc | aat | cgc | cag | 384 |
| Ala | Phe | Pro | Asn | Leu | Lys | Val | Val | Met | Val | Val | Asp | Gly | Asn | Arg | Gln |
| | | | 115 | | | | | 120 | | | | | 125 | | |

| gaa | gat | acc | tac | atg | ttg | gac | atc | ttc | cat | gag | gtg | ctg | ggt | ggc | act | 432 |
| Glu | Asp | Thr | Tyr | Met | Leu | Asp | Ile | Phe | His | Glu | Val | Leu | Gly | Gly | Thr |
| 130 | | | | | 135 | | | | | 140 | | | | | |

| gag | caa | gct | ggc | ttc | ttt | gtg | tgg | cgt | agc | aat | ttc | cat | gag | gcg | ggt | 480 |
| Glu | Gln | Ala | Gly | Phe | Phe | Val | Trp | Arg | Ser | Asn | Phe | His | Glu | Ala | Gly |
| 145 | | | | | 150 | | | | | 155 | | | | | 160 |

| gaa | gga | gag | aca | gag | gcc | agc | ctg | cag | gaa | ggc | atg | gag | cgt | gtg | cga | 528 |
| Glu | Gly | Glu | Thr | Glu | Ala | Ser | Leu | Gln | Glu | Gly | Met | Glu | Arg | Val | Arg |
| | | | | 165 | | | | | 170 | | | | | 175 | |

| gct | gtg | gtg | tgg | gcc | agc | acc | ttc | tca | tgc | atc | atg | cag | aag | tgg | ggg | 576 |
| Ala | Val | Val | Trp | Ala | Ser | Thr | Phe | Ser | Cys | Ile | Met | Gln | Lys | Trp | Gly |
| | | | 180 | | | | | 185 | | | | | 190 | | |

| ggc | aag | cgt | gag | gtc | atg | tac | act | gcc | ttc | aag | gcc | ctt | ggc | aac | tca | 624 |
| Gly | Lys | Arg | Glu | Val | Met | Tyr | Thr | Ala | Phe | Lys | Ala | Leu | Gly | Asn | Ser |
| | | | 195 | | | | | 200 | | | | | 205 | | |

| gtg | gac | tac | atc | cag | gtg | tgt | gac | tct | gac | act | gtg | ctg | gac | cca | gcc | 672 |
| Val | Asp | Tyr | Ile | Gln | Val | Cys | Asp | Ser | Asp | Thr | Val | Leu | Asp | Pro | Ala |
| | 210 | | | | | 215 | | | | | 220 | | | | |

| tgc | acc | att | gag | atg | ctt | cga | gtc | ttg | gaa | gaa | gat | ccc | caa | gta | gga | 720 |
| Cys | Thr | Ile | Glu | Met | Leu | Arg | Val | Leu | Glu | Glu | Asp | Pro | Gln | Val | Gly |
| 225 | | | | | 230 | | | | | 235 | | | | | 240 |

| ggt | gtt | gga | gga | gat | gtc | caa | atc | ctc | aac | aag | tat | gat | tca | tgg | atc | 768 |
| Gly | Val | Gly | Gly | Asp | Val | Gln | Ile | Leu | Asn | Lys | Tyr | Asp | Ser | Trp | Ile |
| | | | | 245 | | | | | 250 | | | | | 255 | |

| tcc | ttc | ctg | agc | agt | gtg | agg | tac | tgg | atg | gct | ttc | aac | gtg | gag | cgg | 816 |
| Ser | Phe | Leu | Ser | Ser | Val | Arg | Tyr | Trp | Met | Ala | Phe | Asn | Val | Glu | Arg |
| | | | 260 | | | | | 265 | | | | | 270 | | |

| gcc | tgc | cag | tcc | tac | ttt | ggc | tgt | gtg | caa | tgt | att | agt | ggg | cct | ttg | 864 |
| Ala | Cys | Gln | Ser | Tyr | Phe | Gly | Cys | Val | Gln | Cys | Ile | Ser | Gly | Pro | Leu |
| | | | 275 | | | | | 280 | | | | | 285 | | |

| ggc | atg | tac | cgc | aac | agc | ctc | ctt | cag | cag | ttc | ctg | gag | gat | tgg | tac | 912 |
| Gly | Met | Tyr | Arg | Asn | Ser | Leu | Leu | Gln | Gln | Phe | Leu | Glu | Asp | Trp | Tyr |
| | 290 | | | | | 295 | | | | | 300 | | | | |

| cat | cag | aag | ttc | cta | ggc | agc | aag | tgc | agc | ttt | ggg | gat | gat | cgg | cac | 960 |
| His | Gln | Lys | Phe | Leu | Gly | Ser | Lys | Cys | Ser | Phe | Gly | Asp | Asp | Arg | His |
| 305 | | | | | 310 | | | | | 315 | | | | | 320 |

| ctt | acc | aac | cga | gtc | ctg | agt | ctt | ggc | tac | cgg | act | aag | tat | aca | gca | 1008 |
| Leu | Thr | Asn | Arg | Val | Leu | Ser | Leu | Gly | Tyr | Arg | Thr | Lys | Tyr | Thr | Ala |
| | | | 325 | | | | | 330 | | | | | 335 | | |

-continued

```
cgc tct aag tgc ctc aca gag acc ccc act agg tac ctt cga tgg ctc    1056
Arg Ser Lys Cys Leu Thr Glu Thr Pro Thr Arg Tyr Leu Arg Trp Leu
        340                 345                 350 aat cag caa acc cgc tgg agc aag tct tac ttt cgg gaa tgg ctc tac    1104
Asn Gln Gln Thr Arg Trp Ser Lys Ser Tyr Phe Arg Glu Trp Leu Tyr
                355                 360                 365 aat tct ctg tgg ttc cat aag cac cac ctc tgg atg acc tat gaa tca    1152
Asn Ser Leu Trp Phe His Lys His His Leu Trp Met Thr Tyr Glu Ser
    370                 375                 380 gtg gtc aca ggt ttc ttc cca ttc ttc ctc att gct aca gtc ata caa    1200
Val Val Thr Gly Phe Phe Pro Phe Phe Leu Ile Ala Thr Val Ile Gln
385                 390                 395                 400 ctt ttc tac cgt ggc cgc atc tgg aac att ctc ctc ttc ctg cta aca    1248
Leu Phe Tyr Arg Gly Arg Ile Trp Asn Ile Leu Leu Phe Leu Leu Thr
                405                 410                 415 gtg cag ctg gtg ggc att atc aag gct acc tat gcc tgc ttc ctt cga    1296
Val Gln Leu Val Gly Ile Ile Lys Ala Thr Tyr Ala Cys Phe Leu Arg
            420                 425                 430 ggc aat gca gag atg atc ttc atg tcc ctc tac tcc ctt ctc tat atg    1344
Gly Asn Ala Glu Met Ile Phe Met Ser Leu Tyr Ser Leu Leu Tyr Met
        435                 440                 445 tcc agc ctc ttg cca gcc aag atc ttt gct att gct acc atc aac aag    1392
Ser Ser Leu Leu Pro Ala Lys Ile Phe Ala Ile Ala Thr Ile Asn Lys
    450                 455                 460 tct ggc tgg ggc act tct ggc agg aaa acc att gtc gtg aac ttc att    1440
Ser Gly Trp Gly Thr Ser Gly Arg Lys Thr Ile Val Val Asn Phe Ile
465                 470                 475                 480 ggc cta atc ccc gtg tcc atc tgg gtg gca gtt ctt cta ggg ggg tta    1488
Gly Leu Ile Pro Val Ser Ile Trp Val Ala Val Leu Leu Gly Gly Leu
                485                 490                 495 gcc tac aca gct tat tgc cag gac ctg ttc agt gag acc gag cta gcc    1536
Ala Tyr Thr Ala Tyr Cys Gln Asp Leu Phe Ser Glu Thr Glu Leu Ala
            500                 505                 510 ttc cta gtc tct ggg gcc atc ctg tat ggc tgc tac tgg gtg gcc ctc    1584
Phe Leu Val Ser Gly Ala Ile Leu Tyr Gly Cys Tyr Trp Val Ala Leu
        515                 520                 525 ctc atg ctg tat ctg gcc att att gcc cgg agg tgt ggg aag aag cca    1632
Leu Met Leu Tyr Leu Ala Ile Ile Ala Arg Arg Cys Gly Lys Lys Pro
    530                 535                 540 gaa cag tat agc ctg gct ttt gcg gag gtg tga                        1665
Glu Gln Tyr Ser Leu Ala Phe Ala Glu Val
545                 550

<210> SEQ ID NO 6
<211> LENGTH: 554
<212> TYPE: PRT
<213> ORGANISM: Mus musculus

<400> SEQUENCE: 6

Met Pro Val Gln Leu Thr Thr Ala Leu Arg Val Gly Thr Ser Leu
1               5                   10                  15

Phe Ala Leu Val Val Leu Gly Gly Ile Leu Ala Ala Tyr Val Thr Gly
                20                  25                  30

Tyr Gln Phe Ile His Thr Glu Lys His Tyr Leu Ser Phe Gly Leu Tyr
            35                  40                  45

Gly Ala Ile Leu Gly Leu His Leu Leu Ile Gln Ser Leu Phe Ala Phe
        50                  55                  60

Leu Glu His Arg Arg Met Arg Arg Ala Gly Arg Pro Leu Lys Leu His
65                  70                  75                  80
```

-continued

```
Cys Ser Gln Arg Ser Arg Ser Val Ala Leu Cys Ile Ala Ala Tyr Gln
             85                  90                  95

Glu Asp Pro Glu Tyr Leu Arg Lys Cys Leu Arg Ser Ala Gln Arg Ile
        100                 105                 110

Ala Phe Pro Asn Leu Lys Val Val Met Val Val Asp Gly Asn Arg Gln
        115                 120                 125

Glu Asp Thr Tyr Met Leu Asp Ile Phe His Glu Val Leu Gly Gly Thr
130                 135                 140

Glu Gln Ala Gly Phe Phe Val Trp Arg Ser Asn Phe His Glu Ala Gly
145                 150                 155                 160

Glu Gly Glu Thr Glu Ala Ser Leu Gln Glu Gly Met Glu Arg Val Arg
                165                 170                 175

Ala Val Val Trp Ala Ser Thr Phe Ser Cys Ile Met Gln Lys Trp Gly
                180                 185                 190

Gly Lys Arg Glu Val Met Tyr Thr Ala Phe Lys Ala Leu Gly Asn Ser
            195                 200                 205

Val Asp Tyr Ile Gln Val Cys Asp Ser Asp Thr Val Leu Asp Pro Ala
210                 215                 220

Cys Thr Ile Glu Met Leu Arg Val Leu Glu Glu Asp Pro Gln Val Gly
225                 230                 235                 240

Gly Val Gly Gly Asp Val Gln Ile Leu Asn Lys Tyr Asp Ser Trp Ile
                245                 250                 255

Ser Phe Leu Ser Ser Val Arg Tyr Trp Met Ala Phe Asn Val Glu Arg
                260                 265                 270

Ala Cys Gln Ser Tyr Phe Gly Cys Val Gln Cys Ile Ser Gly Pro Leu
            275                 280                 285

Gly Met Tyr Arg Asn Ser Leu Leu Gln Gln Phe Leu Glu Asp Trp Tyr
290                 295                 300

His Gln Lys Phe Leu Gly Ser Lys Cys Ser Phe Gly Asp Asp Arg His
305                 310                 315                 320

Leu Thr Asn Arg Val Leu Ser Leu Gly Tyr Arg Thr Lys Tyr Thr Ala
                325                 330                 335

Arg Ser Lys Cys Leu Thr Glu Thr Pro Thr Arg Tyr Leu Arg Trp Leu
            340                 345                 350

Asn Gln Gln Thr Arg Trp Ser Lys Ser Tyr Phe Arg Glu Trp Leu Tyr
        355                 360                 365

Asn Ser Leu Trp Phe His Lys His His Leu Trp Met Thr Tyr Glu Ser
        370                 375                 380

Val Val Thr Gly Phe Phe Pro Phe Phe Leu Ile Ala Thr Val Ile Gln
385                 390                 395                 400

Leu Phe Tyr Arg Gly Arg Ile Trp Asn Ile Leu Leu Phe Leu Leu Thr
                405                 410                 415

Val Gln Leu Val Gly Ile Ile Lys Ala Thr Tyr Ala Cys Phe Leu Arg
            420                 425                 430

Gly Asn Ala Glu Met Ile Phe Met Ser Leu Tyr Ser Leu Leu Tyr Met
        435                 440                 445

Ser Ser Leu Leu Pro Ala Lys Ile Phe Ala Ile Ala Thr Ile Asn Lys
450                 455                 460

Ser Gly Trp Gly Thr Ser Gly Arg Lys Thr Ile Val Val Asn Phe Ile
465                 470                 475                 480

Gly Leu Ile Pro Val Ser Ile Trp Val Ala Val Leu Leu Gly Gly Leu
                485                 490                 495

Ala Tyr Thr Ala Tyr Cys Gln Asp Leu Phe Ser Glu Thr Glu Leu Ala
                500                 505                 510
```

```
Phe Leu Val Ser Gly Ala Ile Leu Tyr Gly Cys Tyr Trp Val Ala Leu
        515                 520                 525

Leu Met Leu Tyr Leu Ala Ile Ile Ala Arg Arg Cys Gly Lys Lys Pro
    530                 535                 540

Glu Gln Tyr Ser Leu Ala Phe Ala Glu Val
545                 550
```